US010427156B2

(12) United States Patent
Peumans et al.

(10) Patent No.: US 10,427,156 B2
(45) Date of Patent: Oct. 1, 2019

(54) FLUID ANALYSIS DEVICE

(71) Applicant: IMEC VZW, Leuven (BE)

(72) Inventors: Peter Peumans, Herfelingen (BE);
Liesbet Lagae, Leuven (BE); Paolo Fiorini, Brussels (BE)

(73) Assignee: IMEC VZW, Leuven (BE)

( * ) Notice: Subject to any disclaimer, the term of this patent is extended or adjusted under 35 U.S.C. 154(b) by 67 days.

(21) Appl. No.: 15/529,424

(22) PCT Filed: Nov. 24, 2015

(86) PCT No.: PCT/EP2015/077439
§ 371 (c)(1),
(2) Date: May 24, 2017

(87) PCT Pub. No.: WO2016/083337
PCT Pub. Date: Jun. 2, 2016

(65) Prior Publication Data
US 2017/0326551 A1  Nov. 16, 2017

(30) Foreign Application Priority Data
Nov. 26, 2014 (EP) ..................... 14194859

(51) Int. Cl.
*B01L 3/00* (2006.01)
*G01N 1/14* (2006.01)
(Continued)

(52) U.S. Cl.
CPC ....... *B01L 3/502715* (2013.01); *B01L 3/5027* (2013.01); *B01L 3/50273* (2013.01);
(Continued)

(58) Field of Classification Search
CPC ............. B01L 3/502715; B01L 3/5027; B01L 3/50273; G01N 1/14; G01N 1/38; G01N 33/39
(Continued)

(56) References Cited

U.S. PATENT DOCUMENTS
5,006,202 A  4/1991 Hawkins et al.
5,385,635 A  1/1995 O'Neill
(Continued)

FOREIGN PATENT DOCUMENTS
EP  2011574 A1  1/2009
WO  98/50154  11/1998
(Continued)

OTHER PUBLICATIONS

PCT International Search Report and Written Opinion, PCT International Application No. PCT/EP2015/077412, dated Mar. 1, 2016, 7 pages.
(Continued)

*Primary Examiner* — Tarun Sinha
(74) *Attorney, Agent, or Firm* — McDonnell Boehnen Hulbert & Berghoff LLP

(57) ABSTRACT

The present disclosure relates to a fluid analysis device which comprises a sensing device for analyzing a fluid sample, the sensing device comprising a micro-fluidic component for propagating the fluid sample and a microchip configured for sensing the fluid sample in the micro-fluidic component; a sealed fluid compartment containing a further fluid, the compartment being fluid-tight connected to the sensing device and adapted for providing the further fluid to the micro-fluidic component when the sealed fluid compartment is opened; and an inlet for providing the fluid sample
(Continued)

to the micro-fluidic component. Further, the present disclosure relates to a method for sensing a fluid sample using the fluid analysis device.

14 Claims, 18 Drawing Sheets

(51) Int. Cl.
   *G01N 1/38* (2006.01)
   *G01N 33/49* (2006.01)

(52) U.S. Cl.
   CPC .............. *G01N 1/14* (2013.01); *G01N 1/38* (2013.01); *G01N 33/49* (2013.01); *B01L 3/502707* (2013.01); *B01L 2200/027* (2013.01); *B01L 2200/10* (2013.01); *B01L 2300/041* (2013.01); *B01L 2300/044* (2013.01); *B01L 2300/046* (2013.01); *B01L 2300/0627* (2013.01); *B01L 2300/0645* (2013.01); *B01L 2300/0672* (2013.01); *B01L 2300/087* (2013.01); *B01L 2300/0816* (2013.01); *B01L 2300/0825* (2013.01); *B01L 2300/0848* (2013.01); *B01L 2300/0867* (2013.01); *B01L 2300/0883* (2013.01); *B01L 2300/0887* (2013.01); *B01L 2300/1827* (2013.01); *B01L 2400/0406* (2013.01); *B01L 2400/049* (2013.01); *B01L 2400/0683* (2013.01); *B01L 2400/086* (2013.01); *G01N 2001/386* (2013.01)

(58) Field of Classification Search
   USPC ........................................... 73/64.56
   See application file for complete search history.

(56) References Cited

U.S. PATENT DOCUMENTS

| | | |
|---|---|---|
| 5,919,712 A | 7/1999 | Herron et al. |
| 6,123,820 A | 9/2000 | Bergkuist et al. |
| 2002/0022261 A1 | 2/2002 | Anderson et al. |
| 2006/0078475 A1 | 4/2006 | Tai et al. |
| 2006/0153736 A1 | 7/2006 | Kalra et al. |
| 2007/0172388 A1 | 7/2007 | Padmanabhan et al. |
| 2009/0090172 A1* | 4/2009 | Angelescu ............ G01N 11/08 73/54.14 |
| 2009/0169427 A1 | 7/2009 | Supriya et al. |
| 2009/0317302 A1 | 12/2009 | McAvoy et al. |
| 2011/0201099 A1 | 8/2011 | Anderson et al. |
| 2013/0189796 A1 | 7/2013 | Kanaley et al. |
| 2014/0322706 A1* | 10/2014 | Kayyem ........... B01L 3/502715 435/6.11 |
| 2015/0093816 A1* | 4/2015 | Lagae ................. G01N 27/227 435/287.2 |

FOREIGN PATENT DOCUMENTS

| | | |
|---|---|---|
| WO | 2012/054904 A2 | 4/2012 |
| WO | 2014/187926 A1 | 11/2014 |

OTHER PUBLICATIONS

PCT International Search Report and Written Opinion, PCT International Application No. PCT/EP2014/060591, dated Sep. 1, 2014, 8 pages.

Lee, Hakho et al., "IC/Microfuidic Hybrid System for Magnetic Manipulation of Biological Cells", IEEE Journal of Solid-State Circuits, vol. 41, No. 6, Jun. 6, 2006, pp. 1471-1480.

PCT International Search Report and Written Opinion, PCT International Application No. PCT/EP2015/077439, dated Feb. 15, 2016, 8 pages.

Tanaka, Hiroyuki et al., "Electrochemical Sensor With Dry Reagents Implemented in Lab-on-Chip for Single Nucleotide Polymorphism Detection", Japanese Journal of Applied Physics, No. 53, Apr. 17, 2014, pp. 1-5.

\* cited by examiner

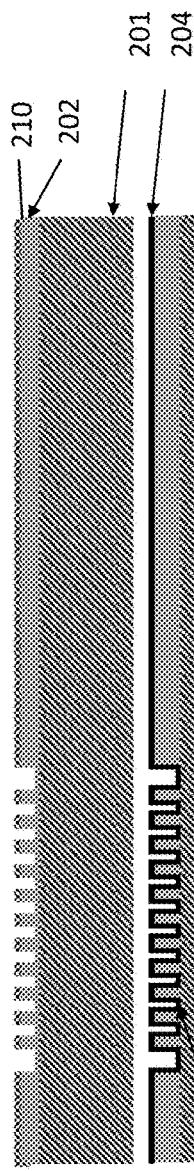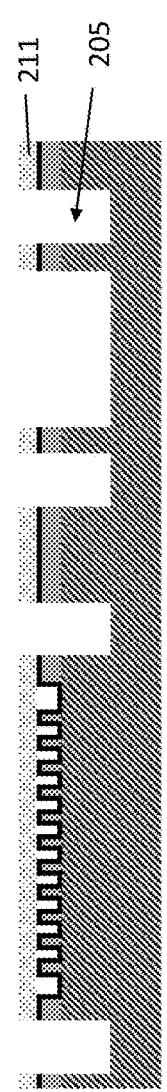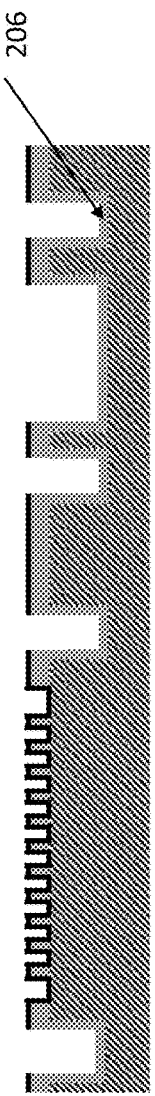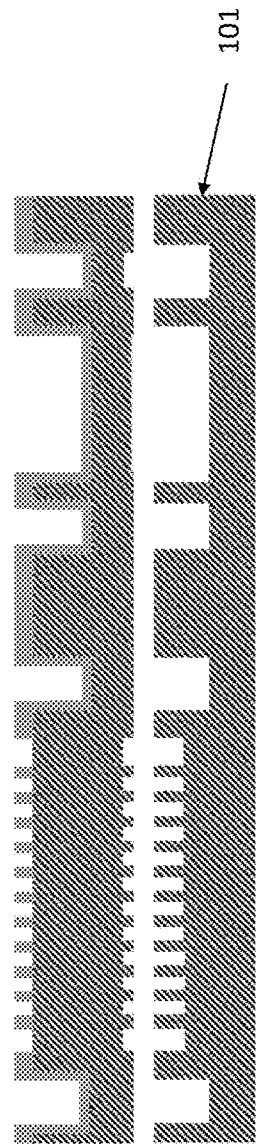
FIG. 11  FIG. 12  FIG. 13  FIG. 14  FIG. 15  FIG. 16  FIG. 17

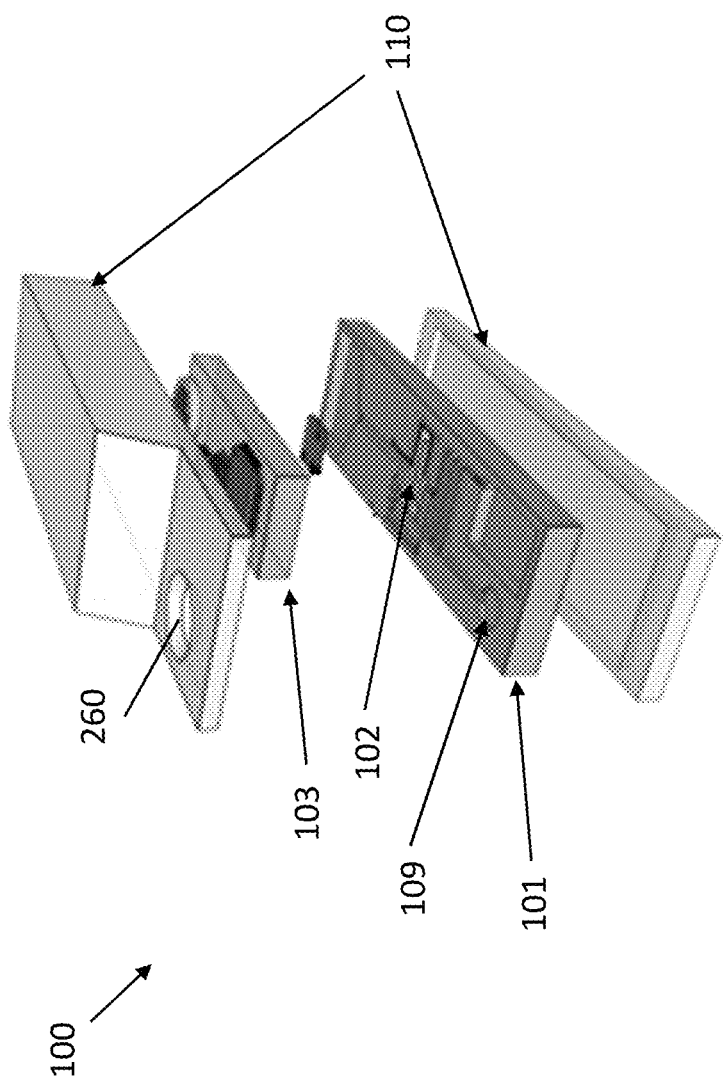

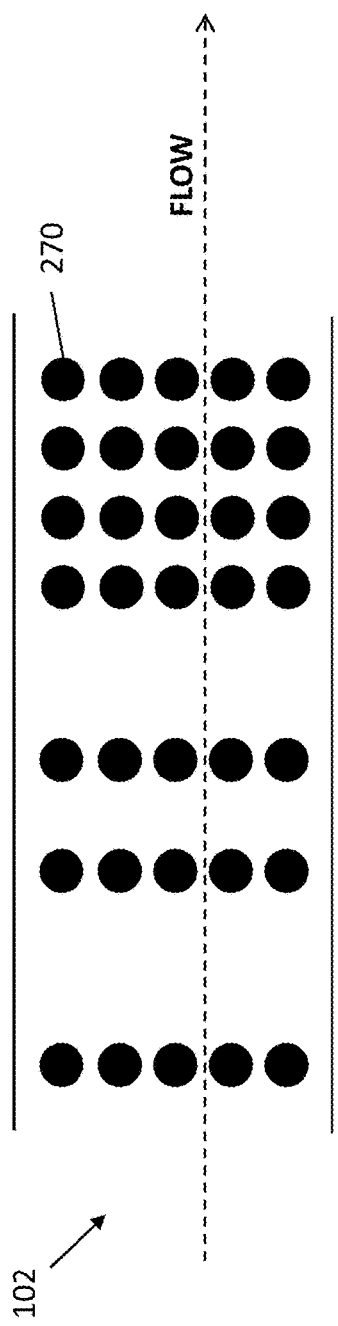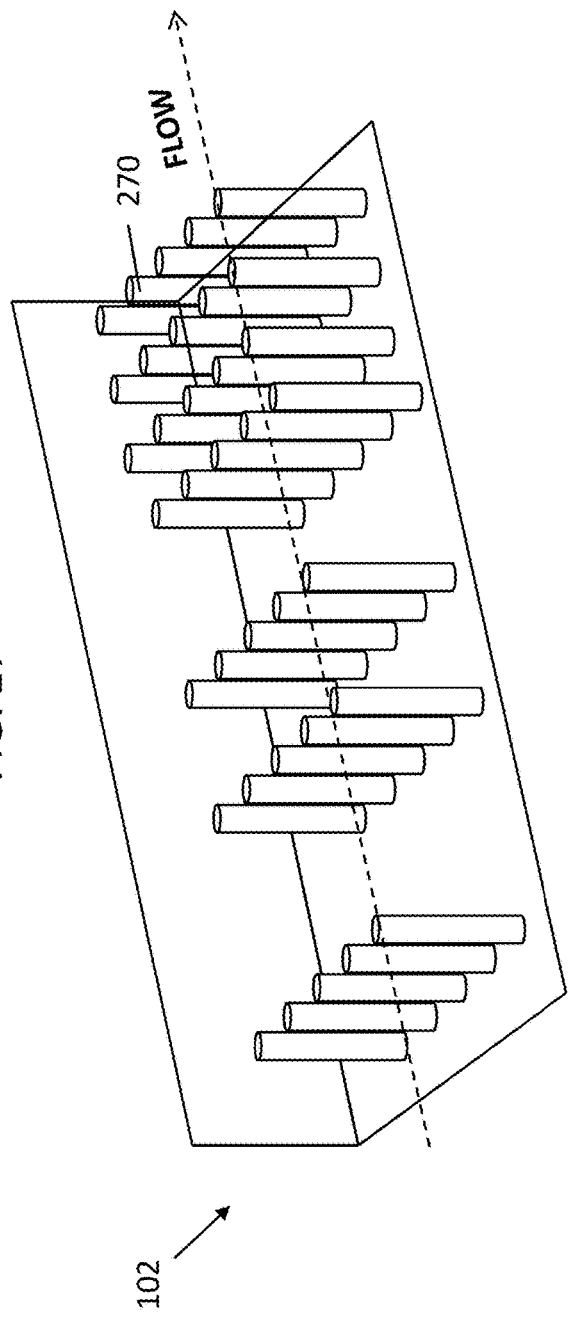

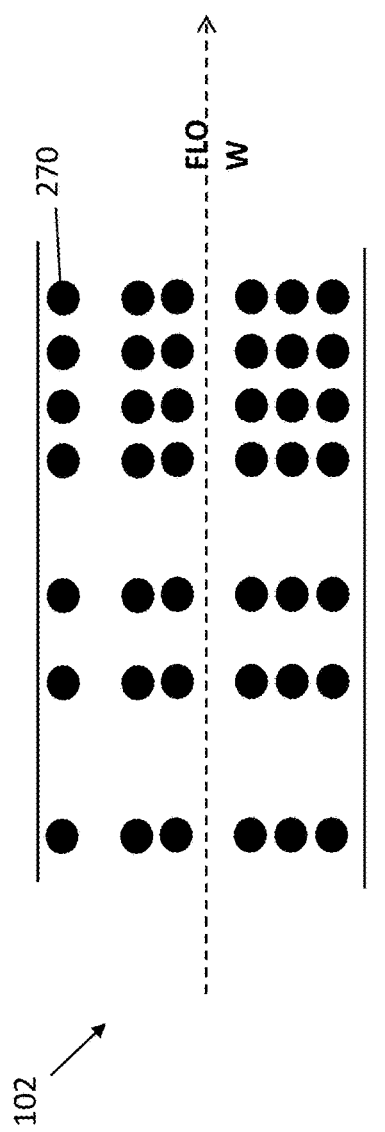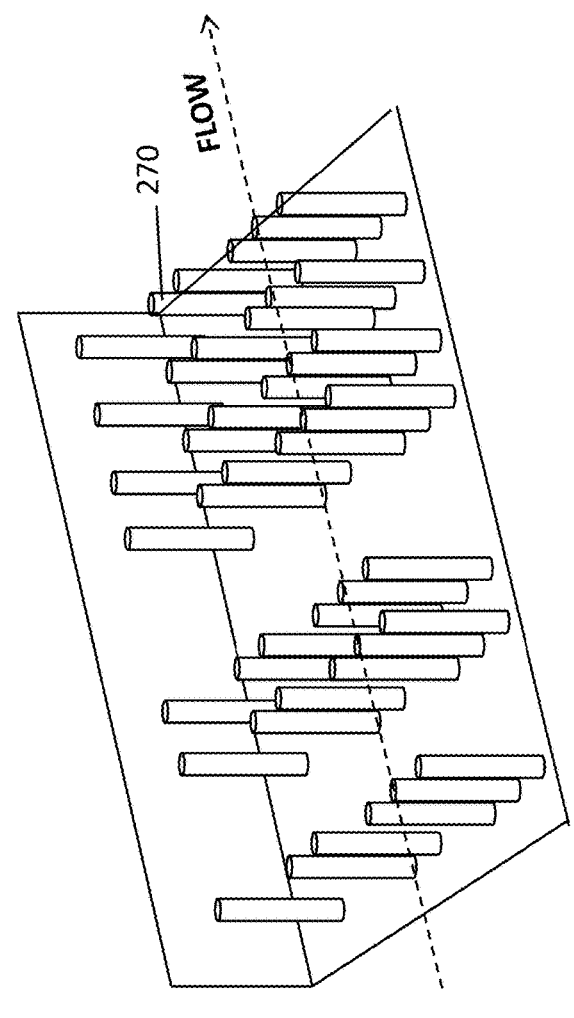

FLUID ANALYSIS DEVICE

CROSS-REFERENCE TO RELATED APPLICATION

The present application is a national stage entry of PCT/EP2015/077439 filed Nov. 24, 2015, which claims priority to European Patent Application No. 14194859.6 filed Nov. 26, 2014, the contents of which are hereby incorporated by reference.

Field of the Disclosure

The present disclosure relates to fluid analysis. In particular, the present disclosure is related to compact devices and methods for the analysis of a fluid sample. More in particular, the present disclosure is related to fully integrated lab-on-a-chip devices for the analysis of fluid samples as well as to corresponding methods for analysis of fluid samples.

Background

Currently, conventional point-of-care devices for the analysis of blood exist. A disadvantage of these devices is their size which depends on the different components needed to perform analysis of blood.

Current disposable devices are typically inserted in expensive read-out instruments; with many nondisposable different electronic or optical components for reading out the biochemical reactions taking place in the disposable. Another disadvantage of conventional point-of-care devices is their cost of fabrication.

Other conventional devices are lateral flow test strips. These test strips are usually fabricated from cellulose which does not allow a precise control of the flow of a fluid sample propagating through the test strips. This narrows the scope of application of these devices.

There is a need for a low-cost, easy to use, disposable, compact device for the fully integrated analysis of a fluid sample.

Summary

The embodiments described herein provide compact devices for analyzing fluid samples as well as corresponding methods for analyzing fluid samples.

The embodiments described herein provide for low-cost devices for analyzing fluid samples, whereby such low-cost devices can, for example, be disposable.

The embodiments described herein provide devices for analyzing fluid samples that are easy to use.

This is accomplished by a method and device according to embodiments described herein.

According to some embodiments, a fluid analysis device is presented, comprising a sensing device for analyzing a fluid sample, comprising a micro-fluidic component for propagating the fluid sample and a microchip positioned and configured for sensing the fluid sample in the micro-fluidic component; a sealed fluid compartment containing a further fluid, fluid-tight connected to the sensing device and adapted for providing the further fluid to the micro-fluidic component when the sealed fluid compartment is opened; and an inlet for providing the fluid sample to the micro-fluidic component.

According to an example embodiment, the fluid analyzing device further comprises a package comprising the sensing device, the sealed fluid compartment and the inlet. The sensing device and the sealed fluid compartment are encapsulated by the package. The inlet is located in the package, e.g. in a wall of the package, down to the micro-fluidic component such that a fluid sample may be provided to the micro-5 fluidic component.

According to an example embodiment, the sealed fluid compartment comprises a sacrificial element adapted to open the sealed fluid compartment towards the micro-fluidic component when the sacrificial element is destroyed.

According to an example embodiment, the fluid analysis device further comprises a movable structure for destructing the sacrificial element. The moveable structure may be a part of the sealed fluid compartment, e.g. integrated in a wall of the sealed fluid compartment, or a part of the package, e.g. integrated in a wall of the package.

According to an example embodiment, the movable structure is a movable puncture device, adapted to destruct the sacrificial element when actuated, e.g. from outside the package.

According to an example embodiment, a part of a wall of the sealed fluid compartment is removable thereby allowing air supply to the sealed fluid compartment. According to an example embodiment, the compartment may alternatively comprise an air supply element, e.g. a venting channel, permanently present and allowing inflow of air when the sacrificial element is destroyed. The air supply element may be provided such that (e.g. through design of the diameters of the microfluidic channels) partial pressures are such that, when the sacrificial element is not destroyed, no air enters the fluid compartment and, when the sacrificial element is destroyed, air enters the fluid compartment. In other words, embodiments of the present disclosure may comprise an air supply element for supplying air to the fluid compartment once the sacrificial element has been destroyed.

According to an example embodiment, the sacrificial element comprises a heating element, e.g. heating resistor, positioned such that the sacrificial element is destroyed by heating, thereby opening the sealed fluid compartment. According to an example embodiment, the heating element is positioned in or on the sacrificial element. According to an example embodiment, the heating element is positioned on a substrate comprising the micro-fluidic component.

According to an example embodiment, the fluid analysis device comprises a fluid detector positioned to detect the fluid sample when provided in the micro-fluidic component, and wherein the sealed fluid compartment is configured to open when the fluid sample is detected. A controller for controlling the opening of the sealed fluid compartment based on the detection of the fluid sample may be provided.

According to an example embodiment, the sealed fluid compartment is configured for activating propagation of the fluid sample in the micro-fluidic component, e.g. by activating a pumping system or by opening a fluid stop, when the sealed fluid compartment is opened.

In an aspect of the disclosure, a method for sensing a fluid sample is presented, comprising: providing a fluid analyzing device according to any of the preceding claims; providing a fluid sample to the micro-fluidic component; mixing the fluid sample with the further fluid that was contained in the sealed fluid compartment by opening the fluid compartment thereby providing the further fluid in the micro-fluidic component; performing sensing on the fluid sample, e.g. the fluid sample mixed with the further fluid, using the sensing device.

According to an example embodiment, the method further comprises detecting a fluid sample being provided to the micro-fluidic component, and opening the sealed fluid compartment when the fluid sample is detected.

In an aspect, the present disclosure relates to a device for analyzing a fluid sample. The device comprises: a fluidic substrate comprising: a micro-fluidic component embedded in the fluidic substrate configured to propagate a fluid sample via capillary force through the micro-fluidic component; and a means for providing a fluid sample connected to the micro-fluidic component; a lid attached to the fluidic substrate at least partly covering the fluidic substrate and at least partly closing the micro-fluidic component. The fluidic substrate is a silicon fluidic substrate and the lid is a CMOS chip.

According to some embodiments, at least a part of the lid is in contact with the fluid sample when the fluid sample is present in the device.

According to some embodiments, the lid comprises a transistor layer, the transistor layer being electrically connected at least one electrical component, the electrical component being at least one of the following: biosensing circuitry, electrodes for sensing purposes, electrodes for fluid manipulation purposes, circuitry for data communication purposes, circuitry for wireless data communication purposes, temperature sensors, heater electrodes for temperature control and fluid sensors and electrodes for fluidic viscosity control, imaging components, e.g. lensfree imaging components. These electrical components may be present on the lid, hence on the microchip. In an embodiment, the transistor layer and the electrical components are integrated in a single microchip.

According to some embodiments, the means for providing a fluid sample is an integrated needle fabricated from silicon and comprising an inner fluidic channel connected to the microfluidic component. The needle is a protruding portion of the fluidic substrate and positioned to penetrate skin tissue when pressed against the skin tissue.

According to some embodiments, the fluidic substrate comprises a cut-out and the needle is positioned in the cut-out.

According to some embodiment, the fluidic substrate comprises a protection structure for protecting the needle, removably attached to the fluidic substrate.

According to some embodiments, the means for providing a fluid sample is an inlet. A sample drop may be inserted into the microfluidic component by means of capillary suction. The microfluidic component may comprise different fluidic compartments, for instance for multi-omic analysis. The different microfluidic compartments can have same or different depths. The different microfluidic compartments may be separated by valves that may be actuated in any suitable way, for instance by fluidic forces or by electricity. Electrodes for actuation may be contained on the fluidic substrate or on the lid.

According to some embodiments, the fluidic substrate or the lid may further comprise at least one optical waveguide to allow optical excitation and sensing of the fluid sample when present in the device. The fluidic substrate or the lid may also comprise filters for rejecting optical excitation from emission to measure a fluorescent signal. The fluidic substrate or the lid may comprise multispectral filters for measuring fluorescent signals with multiple colors. The fluidic substrate or the lid may comprise an optical waveguide and/or a pinhole to irradiate the sample for performing lensfree microscopy.

According to some embodiments, the fluidic substrate or the lid comprises at least one through-hole for application of a biochemical reagent to at least one region of the microfluidic component or to at least one region of the lid.

According to some embodiments, the lid is bonded to the fluidic substrate using a lithographically patterned polymer.

According to some embodiments, the device may further comprise metal contacts electrically connected to the lid for read-out of electrical signals generated by the fluid and captured by measurement systems in the lid. According to some embodiments, the lid of the device may further comprise CMOS active pixels for readout of optical signals from the fluid.

According to some embodiments, at least part of the fluidic substrate and/or the lid is fabricated from a transparent material to allow optical inspection of a fluid sample in the microfluidic component.

According to some embodiments, the shape of the device allows insertion into a mobile handheld communication device, e.g. a smartphone.

In another aspect, some embodiments relate to a method for fabricating a device for analyzing a fluid sample. The method comprises: providing a fluidic substrate; providing a lid; attaching the fluidic substrate to the lid to close the fluidic substrate at least partly. The fluidic substrate is a silicon fluidic substrate and the lid is CMOS chip; and the fluidic substrate is attached to the lid using a CMOS compatible bonding process.

According to some embodiments, providing a fluidic substrate may comprise: providing a silicon substrate, providing a mask layer, for instance an oxide mask, patterning the oxide mask so as to create fine structures in the oxide mask; providing a protection layer to protect the oxide mask; patterning coarse structures; etching of the coarse structures; growing oxide for protecting the coarse structures; removing the protection layer and etch the fine structures; removing the oxide.

According to some embodiments, providing a fluidic substrate may comprise providing a silicon substrate, providing a plurality of masks on top of one another and using each mask for creating microfluidic structures of different depths.

In accordance with some embodiments, providing a fluidic substrate may comprise providing a silicon substrate, providing a first oxide mask, patterning microfluidic structures, etching the substrate to single depth, providing a second oxide mask, patterning microfluidic structures, etching the substrate to a second depth, and, if required, repeating these steps for creating multiple depths of microfluidic structures.

According to some embodiments, the fluidic substrate and the lid of a device according to embodiments of the present disclosure may be part of a larger fluidic package, which may be made from different materials like for instance polymers, and which may contain larger fluidic structures, reagents, fluidic and electrical interfaces. This allows the system to be more cost efficient.

According to some embodiments, surfaces of the fluidic substrate and the lid may be partially or fully coated to modify surface interactions of the substrate with the fluid sample.

In another aspect, the present disclosure provides the use of a sensing device to perform microscopy. Microscopy may be implemented by using the lid for detecting lensfree images according to the principles of digital holography.

The use of the device as described may perform multi-omic analysis in which the fluidic substrate is used for performing multiple assays in multiple channels and chambers, and the CMOS lid is used to detect multiple signals from all assays. Those signals can combine multiple DNA, RNA, small molecule, cell signals from a same analyte.

In some embodiments, the device is used as a single use disposable device for analysis of a small amount of fluid.

In another aspect, the data from the lid may be sent to a smart device, for instance using a wireless connection. The smart device can be used for processing, visualizing and/or transferring the data.

In some embodiments, the combined data gathered from a single same sample may be used in a software algorithm for calculating a parameter correlating to disease or well-being of an individual.

Some aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE FIGURES

The above, as well as additional, features will be better understood through the following illustrative and non-limiting detailed description of example embodiments, with reference to the appended drawings.

FIG. 11-FIG. 17 illustrate a method to fabricate a fluidic substrate for use in a device, according to an example embodiment.

FIG. 26 illustrates a 3D view of a wireless stand-alone device, according to an example embodiment.

FIG. 27 illustrates a top view of a part of a micro-fluidic component for use in a device, the micro-fluidic component comprising micro-pillars, according to an example embodiment.

FIG. 28 illustrates a 3D view of a part of the micro-fluidic component of FIG. 27, according to an example embodiment.

FIG. 29 illustrates a top view of a part of a micro-fluidic component for use in a device, the micro-fluidic component comprising micro-pillars, according to an example embodiment.

FIG. 30 illustrates a 3D view of a part of the micro-fluidic component of FIG. 29, according to an example embodiment.

Figure 1:
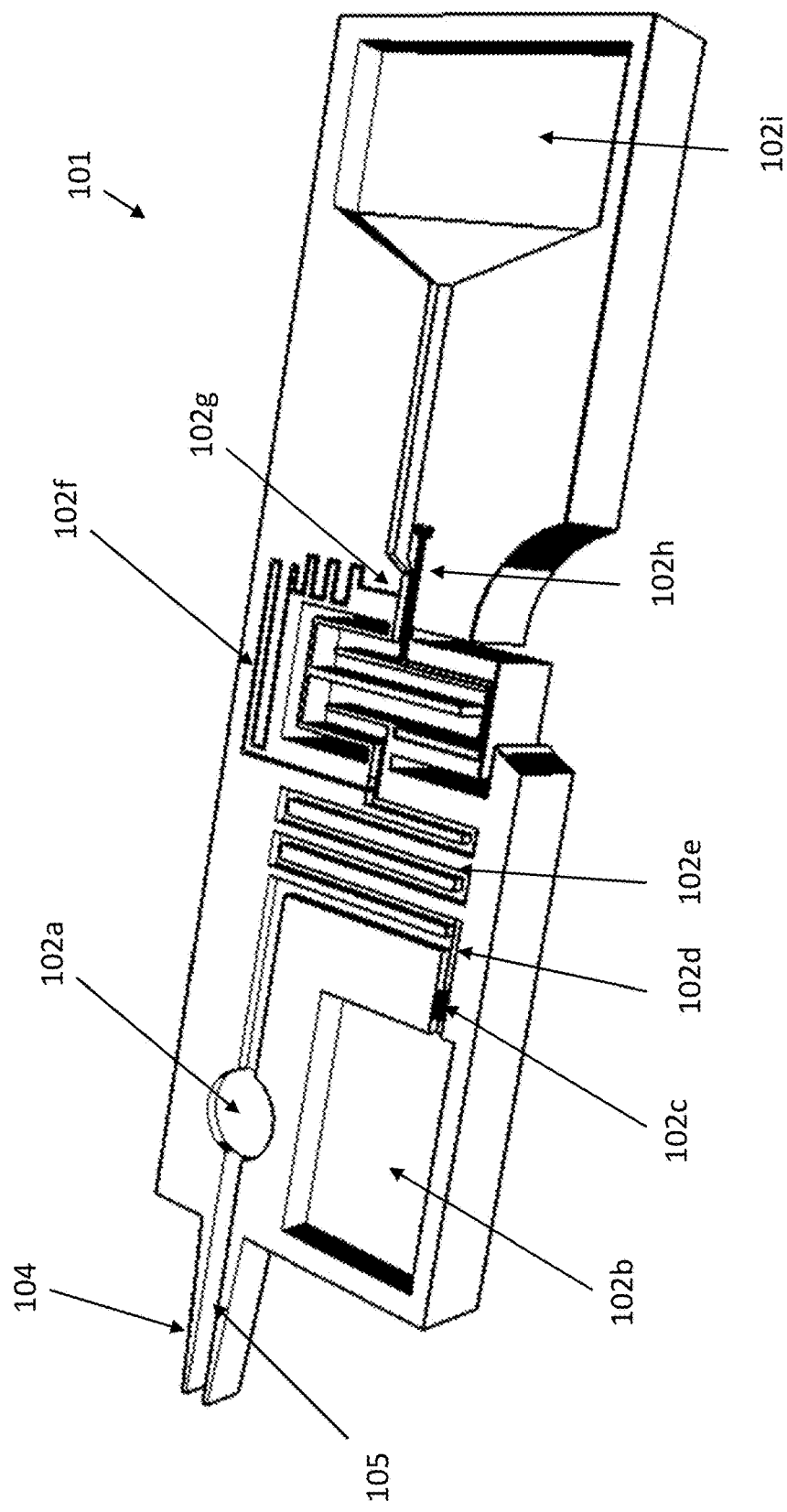
FIG. 1 illustrates a 3D view of a fluidic substrate, according to an example embodiment.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

All the figures are schematic, not necessarily to scale, and generally only show parts which are necessary to elucidate example embodiments, wherein other parts may be omitted or merely suggested.

DETAILED DESCRIPTION OF THE ILLUSTRATIVE EMBODIMENTS

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments, various features are sometimes grouped together in a single embodiment, figure, or description thereof for the purpose of streamlining the disclosure and aiding in the understanding of one or more of the various aspects. This method of disclosure, however, is not to be interpreted as reflecting an intention that the claimed embodiments require more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art.

For example, in the following claims, any of the claimed embodiments can be used in any combination.

In the description provided herein, numerous specific details are set forth. However, it is understood that some embodiments may be practiced without these specific details. In other instances, well-known methods, structures and techniques have not been shown in detail in order not to obscure an understanding of this description.

In some embodiments, where reference is made to an "I/O pad" or an "I/O contact", reference is made to a contact such as a metal contact allowing input and output of electrical signals of a micro-chip.

In some embodiments, where reference is made to "CMOS", reference is made to Complementary Metal-Oxide Semiconductor technology.

Throughout the description reference is made to "fluid sample". This may refer to biological fluids including but not limited to body fluids, such as blood, serum, urine, gastric and digestive juices, tears, saliva, stool, semen, and interstitial fluids derived from tumorous tissues.

According to an aspect of the disclosure, a fluid analyzing device 1 is presented. The fluid analyzing device 1 comprises a sensing device 100 which is adapted for analyzing a fluid sample. The sensing device 100 comprises a micro-fluidic component 4 for propagating the fluid sample to a microchip 103 present in the sensing device 100. The fluid analyzing device 1 further comprises an inlet 7 for providing the fluid sample to the micro-fluidic component 4. Further, the fluid analyzing device comprises a sealed fluid compartment 6 containing a further fluid which is fluid-tight connected or attached to the sensing device 100. Where reference is made to a further fluid, this may be e.g. a liquid. The micro-fluidic component 4 is embedded in a substrate, e.g. a glass or silicon substrate, and is at least open at the location where the sealed fluid compartment 6 is fluid tight connected to the sensing device 100. By opening the sealed fluid compartment 6 at the side attached to the sensing device 100, the contained further fluid can be provided to the micro-fluidic component 4. The contained further fluid may for example be a buffer solution. The contained further fluid may for example contain fluorophores configured for binding an analyte. By using a sealed fluid compartment 6 separate from the sensing device 100, the substrate comprising the microfluidic component 4 can be smaller thereby reducing cost and contributing to compactness. The micro-fluidic component has been referred to with reference number "4" or with reference number "102" in the present description.

According to an example embodiment, the fluid analyzing device 1 further comprises a package 2 comprising the sensing device 3, the sealed fluid compartment 6 and the inlet 7. The package 2 encapsulates the sensing device 100, the sealed fluid compartment 6 and protects the fluid analyzing device 1 from the environment. For example, the package may be dust, water or shock proof. The package may be fabricated from a resilient material, e.g. a plastic. The inlet 7 in the package 2 is fluidically connected to the inlet of the micro-fluidic component 4. Via the inlet 7 of the package 2, a fluid sample can be provided to the micro-fluidic component 4. If the micro-fluidic component 4 comprises multiple inlets, the package 2 may also comprise multiple corresponding inlets.

Figure 36:
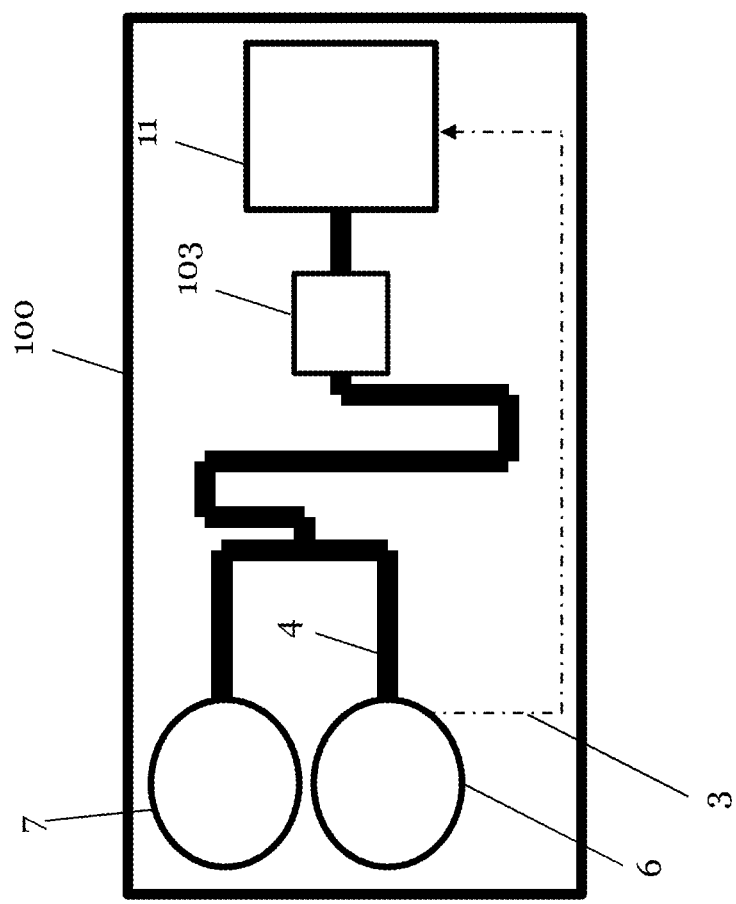
FIG. 36 illustrates a sensing device, according to an example embodiment.

According to an example embodiment, the micro-fluidic component 4 is fluidically connected on one end with the inlet 7. That end may also be fluidically connected with the sealed fluid compartment 6, when the compartment 6 is opened. This is illustrated in FIG. 36.

According to an example embodiment, the sealed fluid compartment 6 may be further configured to initiate or activate propagation of the fluid sample through the micro-fluidic component 4 when the sealed fluid compartment 6 is opened. For example by activating a means for propagating a fluid sample through the micro-fluidic component 4 such as a pump 11, e.g. a capillary pump, or a vacuum compartment 11 which is adapted to propagate the fluid sample through the micro-fluidic component 4.

This way, a fluid sample provided to the sensing device 100 may be mixed with the further fluid, previously contained in the sealed fluid compartment 6, within the micro-fluidic component 4. This enhances the usability of the device. Because the fluid sample is mixed with a further fluid inside the micro-fluidic component 4, by opening the sealed fluid compartment 6, a separate inlet for providing the further fluid externally is not required. Thus, a device with a single inlet is sufficient for sensing a fluid sample. In some example embodiments, the only actions required by the user are: 1) providing the fluid sample to the micro-fluidic component 4, and 2) opening the sealed fluid compartment 6 such that the contained further fluid is provided in the micro-fluidic component 4 and such that a means for propagating the fluid sample is activated. The sealed fluid compartment 6 may also be fluidically connected along the micro-fluidic component 4.

According to an example embodiment, the sealed fluid compartment 6 is part of the sensing device 100. For example, the sealed fluid compartment 6 may be a compartment located in a substrate that also comprises the micro-fluidic component 4. In such an embodiment, the sealed fluid compartment may be a sealed cavity in the substrate which may be fluidically connected to the micro-fluidic component by breaking the seal which seals the cavity. The seal may be a membrane which may be destroyed by heating or by applying pressure.

According to an example embodiment, for reducing cost and to minimize the usage of substrate material, the sealed fluid compartment 6 may be a separate component which is attached to the sensing device 100. According to an example embodiment, the sealed fluid compartment may also be a part of the package 2, e.g. attached inside the package, e.g. attached to an inner wall of the package 2.

According to some embodiments, the sealed fluid compartment 6 comprises a sacrificial element 8 which is adapted to open the sealed fluid compartment 6 toward the micro-fluidic component 4 when the element 8 is destroyed. The sacrificial element 8 is located such that when the element is destroyed, the further fluid is released in the micro-fluidic component 4 while still ensuring a fluid-tight connection to the sensing device to prevent leakage. The sacrificial element 8 may be a membrane, e.g. a sealing foil. In between the sensing device 100 and the sealed fluid compartment 6 a gasket may be present to prevent leakage.

According to an example embodiment, the sacrificial element 8 comprises a heating resistor positioned such that the sacrificial element 8 is destroyed by heating when the heating resistor is electrically driven, thereby opening the sealed fluid compartment 6. According to an example embodiment, the heating resistor is positioned in or on the sacrificial element. According to an example embodiment, the heating resistor is positioned on the sensing device 100, for example on the substrate which comprises the micro-fluidic component 4. The heating resistor may be in direct contact with the sacrificial element 8. In such an embodiment, the heating resistor may be isolated from other parts of the substrate to minimize heat transfer to other components on the substrate. For example, the sensing device 100, e.g. the substrate comprising the micro-fluidic component 4, may comprise trenches located around the heat resistor to isolate the resistor from the rest of the sensing device 100.

Figure 34:
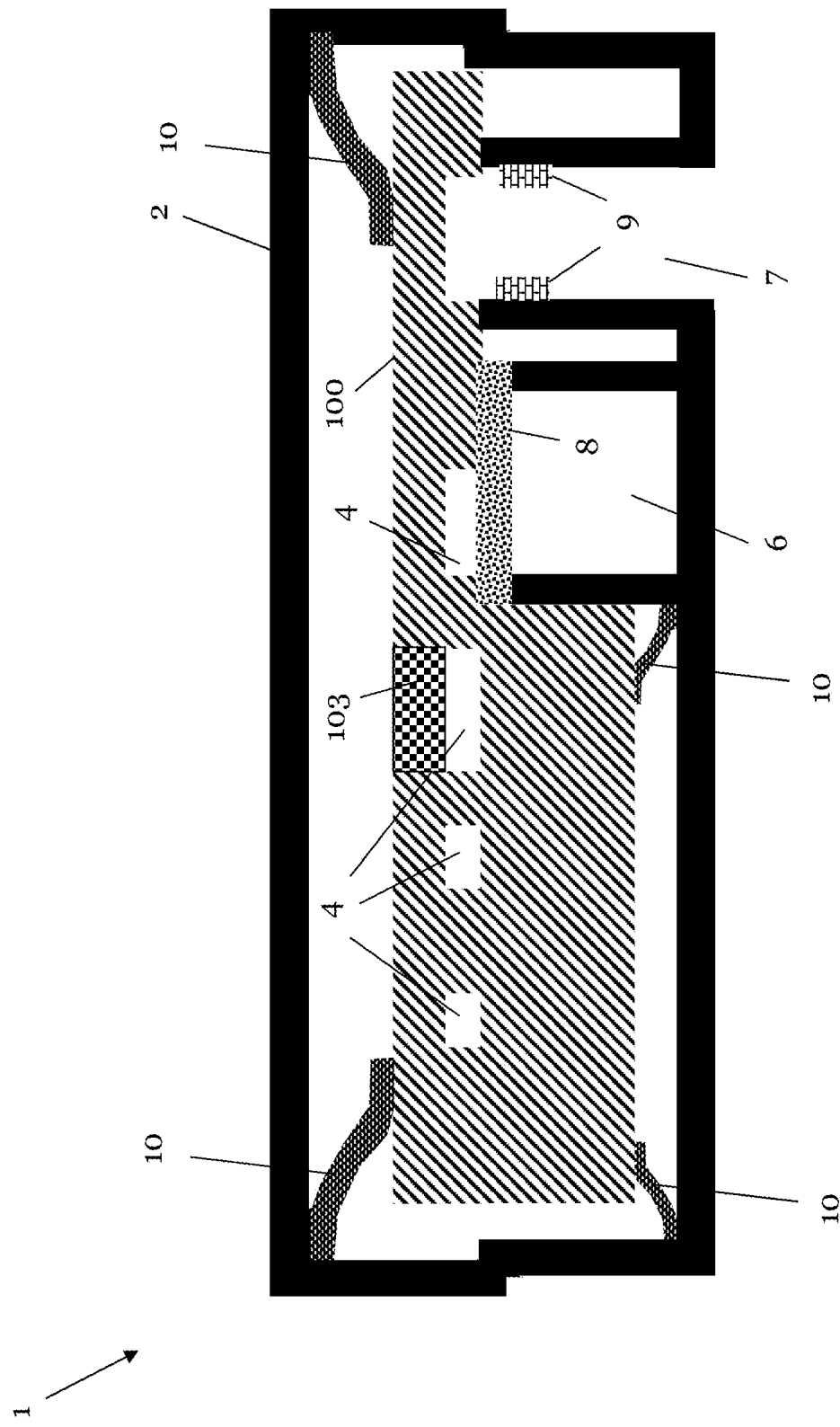
FIG. 34 illustrates a fluid analyzing device having a fluid compartment, according to an example embodiment.

An example embodiment is illustrated in FIG. 34. A package 2 encapsulates a sensing device 100. This package is not essential. The sensing device 100 is fixed inside the package 2, e.g. via clamps 10. The sensing device 100 is positioned inside the package 2 such that a fluid sample introduced in the inlet 7 can enter the micro-fluidic component 4, e.g. via an inlet of the micro-fluidic component 4. A sealed fluid compartment 6 is attached to the sensing device 100. A microchip 103 is part of the sensing device 100 and is positioned such that it may perform direct sensing on a fluid sample inside the microfluidic component 4. The inlet 7 and the sealed fluid compartment 6 are connected to the micro-fluidic component 4. The sacrificial element 8 is positioned in between the sealed fluid compartment 6 and an inlet of the micro-fluidic component 4. When the sacrificial element 8 is removed, the further fluid contained in the sealed fluid compartment 6 can enter the micro-fluidic component 4. The micro-chip 103 is located along the micro-fluidic component 4, such that a fluid sample introduced in the inlet 7 and propagated through the micro-fluidic component 4 passes the micro-chip 103.

According to an example embodiment, the package 2 or the sealed fluid compartment 6 may comprise a movable structure 5 suitable for destructing the sacrificial element 8. The movable structure 5 may be a movable puncture device, positioned and adapted to destruct the sacrificial element 8 when actuated from outside the package or from outside the sealed fluid compartment 6. The moveable puncture device may be integrated in a wall of the sealed fluid compartment 6. The moveable puncture device may be integrated in a wall of the package 2. The moveable puncture device is configured to allow leakage-free actuation of the moveable puncture device. Hence, when the moveable puncture device is actuated, no leakage of the fluid sample via the moveable puncture device occurs. A diaphragm, e.g. fabricated from an elastic material, may be used which allows movement of the puncture device without causing leakage in the sealed fluid compartment 6. Alternatively, a mechanical structure may be used which allows movement of the puncture device and which also preserves the fluid tight connection and ensures that no leakage occurs when the puncture device is moved. The moveable puncture device may comprise a needle which may be located inside the sealed fluid compartment 6. Hence, by moving the puncture device, the needle can be moved towards the sacrificial element 8 such that the sacrificial element 8 can be punctured when applying enough pressure to the moveable puncture device. This causes the sealed fluid compartment 6 to release its content to the micro-fluidic component 4. The mechanical structure may comprise a spring which causes the mechanical structure to return to its initial position when the mechanical structure is not actuated.

Figure 35:
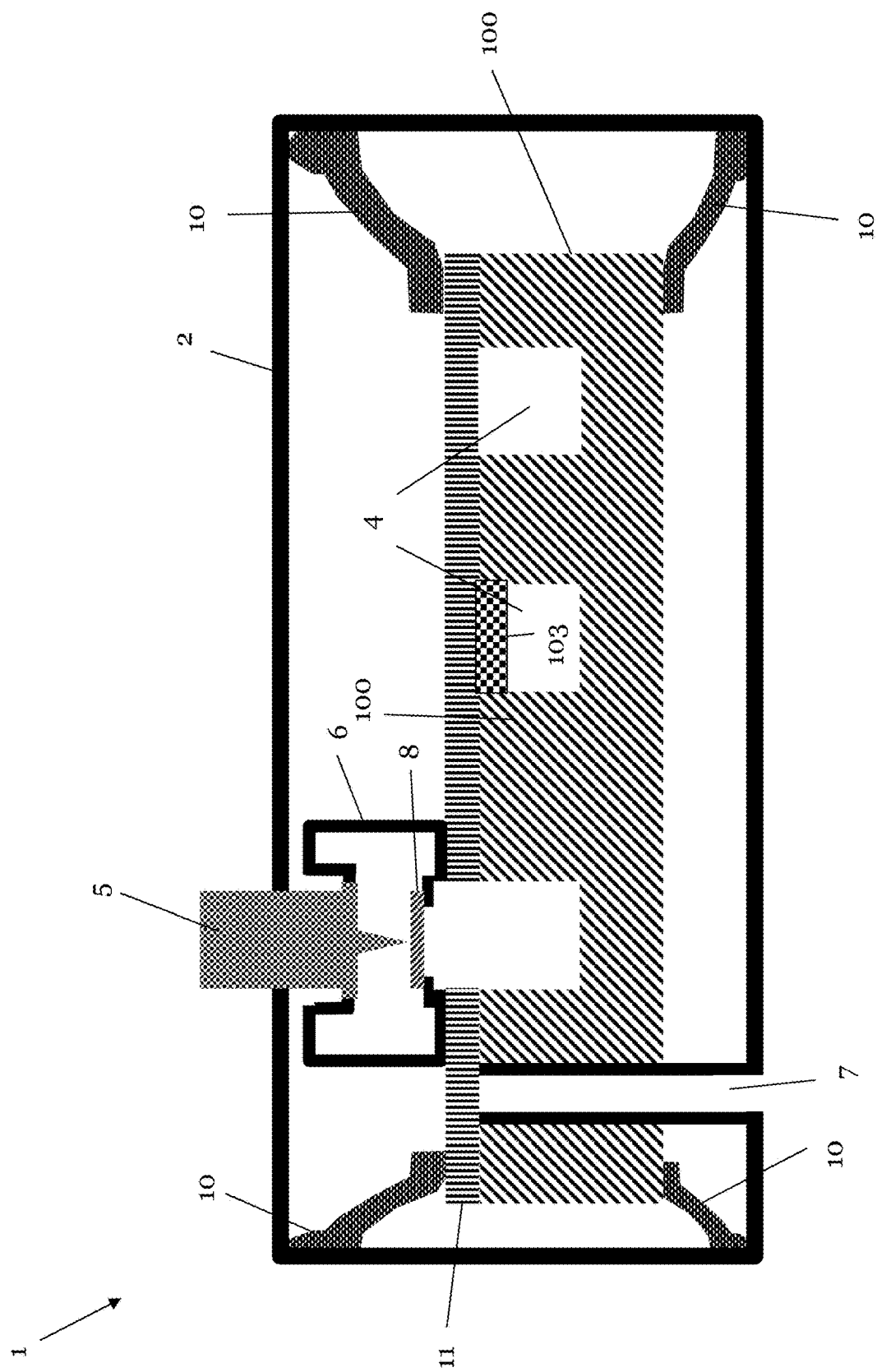
FIG. 35 illustrates a fluid analyzing device having a fluid compartment, according to an example embodiment.

Such an embodiment is illustrated in FIG. 35. A package 2 encapsulates a sensing device 100.

The sensing device 100 is fixed inside the package 2, e.g. via clamps 10. The sensing device 100 is positioned inside the package 2 such that a fluid sample introduced in the inlet 7 can enter the micro fluidic component 4. A sealed fluid compartment 6 is attached to the sensing device 100. In between the sensing device 100 and the sealed fluid compartment 6, a sealing layer 11 is present to bond the sealed fluid compartment 6 to the sensing device 100. The sealing layer may be a layer comprising a polymer.

This sealing layer is optional. The sealed fluid compartment 6 may also be clamped to the sensing device 100. A gasket may be present in between the sealed fluid compartment and the sensing device 100 to avoid leakage. A microchip 103 is located in the sensing device 100 such that it can perform direct sensing on a fluid sample inside the micro-fluidic component 4. The inlet 7 is fluidically connected to one end of the micro-fluidic component 4. In between the sealed fluid compartment 6 and the sensing device 100 a sacrificial element 8 present which allows the sealed fluid compartment to be fluidically and fluid tight connected to the micro-fluidic component 4 when it is removed or broken. The micro-chip 103 is located along the micro-fluidic component 4 such that a fluid sample introduced in the inlet 7 may pass the microchip 103 for sensing purposes when propagated. The sealed fluid compartment 6 can be opened by actuating the moveable puncture device 6 from outside the package 2. When the puncture device 5 is actuated/pushed by a user, the puncture device 5 approaches the sacrificial element 8 and eventually punctures the sacrificial element 8 thereby opening the sealed fluid compartment 6.

According to an embodiment; the actuation of the moveable puncture device triggers a means for propagating a fluid sample through the micro-fluidic component 4. This is illustrated in FIG. 36 with dashed line 3. A pump 11 or a vacuum compartment 11 is activated which creates a suction force in the micro-fluidic component 4 thereby forcing the fluid sample to propagate through the micro-fluidic component 4, until it reaches at least the microchip 103.

According to an example embodiment, the fluid analyzing device 1 further comprises a fluid detector 9 which is positioned to detect the fluid sample when provided in the micro-fluidic component 4. The sealed fluid compartment 6 may be configured to open when the fluid sample is detected. For example, the sacrificial element 8 is removed when the fluid sample is detected. For example, when a fluid sample is detected, the fluid detectors 9 may generate an electrical signal which may be used to trigger the sacrificial element to be removed. The fluid detectors may be one or more electrical element, e.g. electrodes, configured to detect a fluid sample based on impedance or capacitance measurements. The electrodes may be positioned inside the inlet 7. The electrodes may be positioned on the sensing device 100, e.g. in the micro-fluidic component 4.

According to an example embodiment, the fluid analyzing device 1 further comprises a switch or a push-button for activating the fluid analyzing device 1. The switch may be used to electrically connect the fluid analyzing device 1 to an on-board energy source, e.g. a battery. The switch may be adapted such that the sacrificial element 8 is electrically driven when the switch is actuated. When electrically driving the sacrificial element 8, the sealed fluid compartment 6 is opened.

According to an example embodiment, the movable puncture device 5 for breaking the sacrificial element 8 functions as the switch. Hence, the moveable puncture device has a dual functionality being: 1) the moveable puncture device is used to break the sacrificial element and 2) the moveable puncture device is used to start propagation of the fluid sample through the micro-fluidic component 4.

It will be understood that further features and advantages may correspond with one or more features of the sensing device described in further aspects below. Such one or more features may be applied mutates mutandis in embodiments of the sensing device of the present aspect.

In an aspect of the disclosure, a method for sensing a fluid sample is presented, comprising: providing a fluid sensing device 1 according to an aspect of the disclosure; providing a fluid sample to the micro-fluidic component 4; providing the further fluid in the micro-fluidic component 4 by opening the sealed fluid compartment 6 thereby mixing the fluid sample with the further fluid; performing sensing on the mixed fluid sample using the sensing device 100. According to an example embodiment, the movable puncture device is actuated such that the sealed fluid compartment is opened thereby releasing its content to the micro-fluidic component 4. According to an example embodiment, the sealed fluid compartment 6 is opened only when the fluid sample is detected.

An aspect the present disclosure relates to a sensing device 100 for analyzing a fluid sample, as for instance illustrated in FIG. 26. It is to be noticed that features of this aspect may be implemented in the sensing device as described for the first aspect. The sensing device 100 comprises: a fluidic substrate 101 and a lid 103 attached to the fluidic substrate 101 at least partly covering the substrate 101. The fluidic substrate 101 comprises a micro-fluidic component 102 (illustrated by a plurality of microfluidic components such as a sample pad 102a (=an inlet), a reagent storage 102b, a one-time usage hermetic valve 102c, a first trigger valve 102d, a mixer 102e, a delay line 102f, a second trigger valve 102g, an heater 102h and a wick 102i) embedded in the fluidic substrate 101 configured to propagate a fluid sample via capillary force through the micro-fluidic component 102; and a means for providing a fluid sample connected to the micro-fluidic component 102. The lid 103, by at least partly covering the substrate 101, at least partly closes the micro-fluidic component 102. In some embodiments, the fluidic substrate 101 is a silicon fluidic substrate; and the lid 103 is a CMOS chip.

As the fluidic substrate 101 is a silicon substrate and the lid 103 is a CMOS chip, both can be manufactured using mass production compatible silicon process technologies. Cheap CMOS packaging techniques may be used to bond the silicon substrate to the CMOS chip. This reduces the total cost of the sensing device 100 and allows it to be used as a disposable device and produced in high volume. Alternatively, the fluidic substrate 101 is a glass substrate.

FIG. 1 illustrates a 3D view of an embodiment of a fluidic substrate 101.

Figure 3:
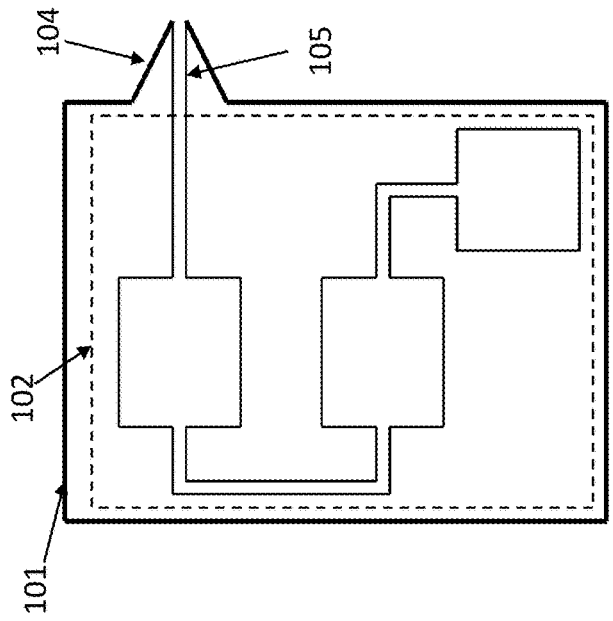
FIG. 3 illustrates a top view of a fluidic substrate used in the device of FIG. 2.
Figure 2:
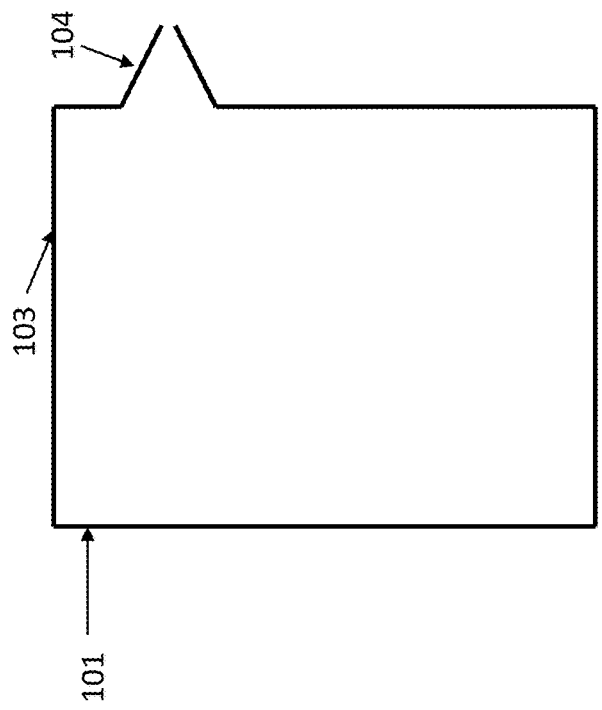
FIG. 2 illustrates a top view of a device for analyzing a fluid sample, according to an example embodiment.
Figure 4:
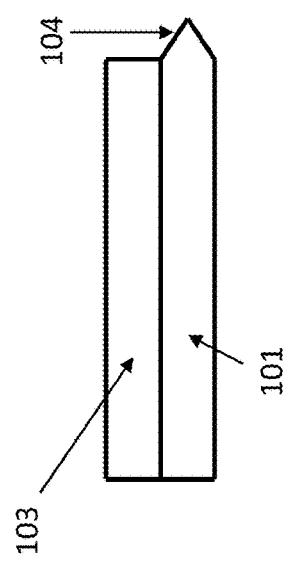
FIG. 4 illustrates a side view of the device of FIG. 2.

A top view of an embodiment of the sensing device 100 is illustrated in FIG. 2, the fluidic substrate 101 and the lid 103 are attached to one another. A top view of an exemplary fluidic substrate 101 used in the sensing device 100 of FIG. 2 is illustrated in FIG. 3. A side view of an embodiment of the sensing device 100 of FIG. 2 where the fluidic substrate 101 is attached to the lid 103 is illustrated in FIG. 4.

A sensing device 100 comprises a fluidic substrate 101 which is attached or bonded to a lid 103. The fluidic substrate 101 comprises a micro-fluidic component 102. The micro-fluidic component 102 may comprise micro-fluidic channels, micro-reactors or other micro-fluidic parts/structures which are interconnected to allow a fluid sample to propagate through the complete micro-fluidic component 102. The micro-fluidic component 102 may comprise a plurality of micro-pillars or microstructures at regular or irregular distances to allow filtering and separation, valving (=function as a valve), mixing of a fluid sample during capillary flow. FIG. 27 illustrates a top view of a part of an open micro-fluidic component 102 comprising micro-pillars 270 to allow filtering and separation, valving, mixing of a fluid sample during capillary flow. FIG. 28 illustrates a 3D view of the open micro-fluidic component 102 of FIG. 27 comprising micro-pillars 270. The micropillars 270 in FIG. 27 and FIG. 28 are positioned as to form a gradient.

This gradient allows the filtering out of larger particles in a first part of the micro-fluidic component 102 and the filtering out of smaller particles in a second part of the micro-fluidic component 102. FIG. 29 and FIG. 30 illustrate another embodiment of a gradient of micro-pillars 270 in the micro-fluidic component 102. The micro-fluidic component 102 may be configured to create a capillary action to propagate a fluid sample through the sensing device 100.

The dimensions of the micro-fluidic component 102 may be adapted to create a capillary action in the micro-fluidic component 102 when a fluid sample is present. For example, dimensions and distance between micro-pillars 270 in the micro-fluidic component 102 may be configured to create a capillary action in the micro-fluidic component 102. The sensing device 100 does not need additional active components (e.g. an active pump) to propagate a fluid sample through the sensing device 100. Thus, the complexity of the sensing device 100 is reduced compared to conventional implementations, which reduces fabrication cost and power consumption. As the costs to fabricate are low, the device may be used as a disposable fluid analysis device.

Some embodiments allow for precise control over the flow of a fluid sample in the micro-fluidic component 102 may be achieved by e.g. correctly dimensioning the micro-fluidic channels and/or micro-pillar sizes and distances which are present in the micro-fluidic component 102. Lithographic patterning may be used to fabricate the micro-fluidic component 102 in the fluidic substrate 101. The lithographic patterning of micro-pillars and micro-fluidic channels of the micro-fluidic component 102 allows to accurately control the dimensions, size and shape of the micro-pillars and micro-fluidic channels, thereby precisely controlling the capillary flow. This precise control over the dimensions, achievable via lithographic processes allows for more reproducible lateral flow than conventional lateral flow test strips, which are made from porous paper with uncontrolled lateral flow. By varying the dimensions over the length of the sensing device 100 it is possible to slow down and/or to increase the speed of the flow of a fluid sample where desired. This allows implementation of more complex biochemical reactions than the simple flow used in existing lateral flow immunoassay tests. The combination with the functions implemented in the CMOS chip bonded as a lid onto the fluidic substrate 101 further adds temperature control, electrical fluid actuation and valving, integrated biosensing and read out where needed. Therefore it becomes possible to implement complex assays, including DNA/RNA assays, proteins, small molecules and cells and combinations thereof in one integrated capillary system starting from body fluids. Moreover, the implementation of capillary flow in silicon with controlled lateral flow and with control over the temperature and flow rate results in more accurate point of care test results.

In some embodiments, the fluidic substrate 101 comprises a means for providing a fluid sample which is connected to the micro-fluidic component 102.

Figure 25:
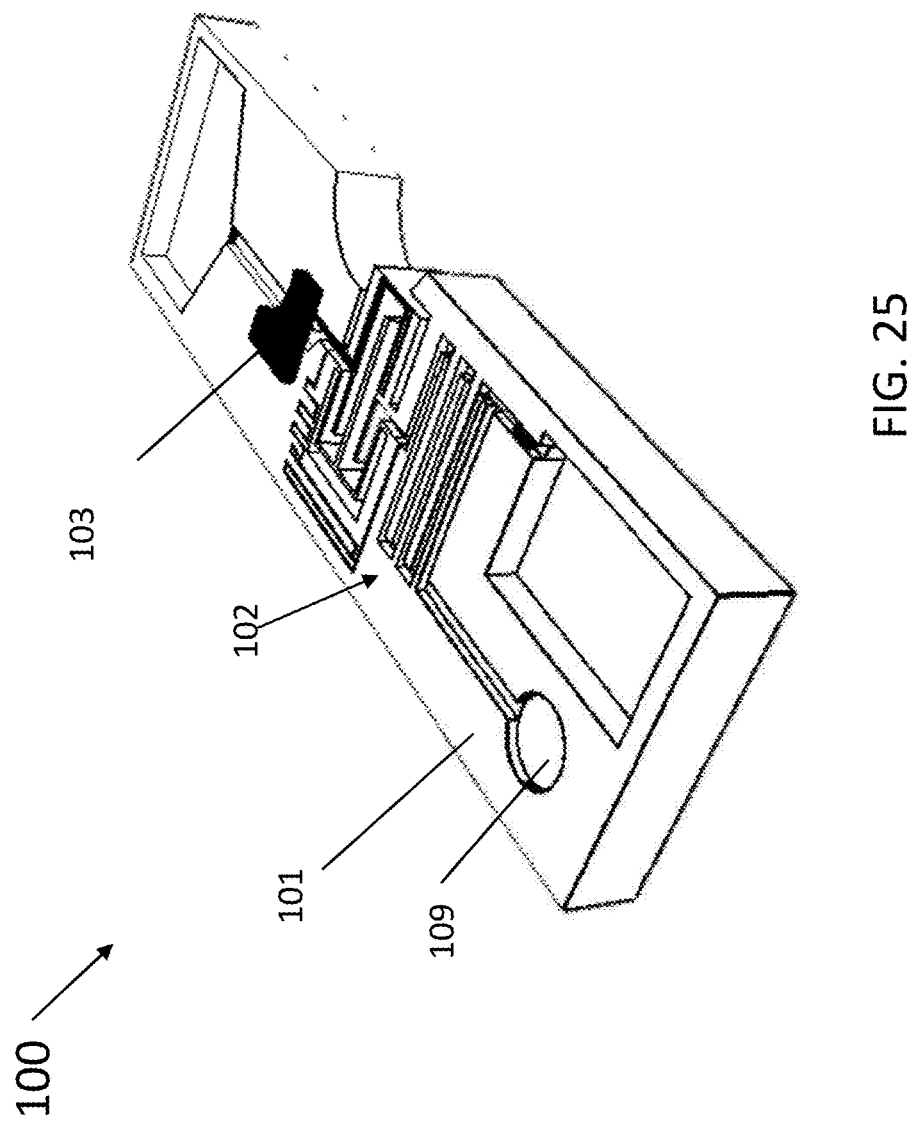
FIG. 25 illustrates a 3D view of a device, according to an example embodiment.

The lid 103 functions as a cover for the fluidic substrate 101 wherein the lid 103 fully or partly closes the micro-fluidic component 102. FIG. 25 illustrates an example embodiment wherein the lid 103 partly covers the fluidic substrate 101. The micro-fluidic component 102 may be an open micro-fluidic component 102 in the fluidic substrate 101. According to alternative embodiments, the dimensions of the lid 103 may be identical to the dimensions of the fluidic substrate 101. The lid 103 may fully or also partially covering the fluidic substrate 101. When the means for providing a fluid sample is an inlet 109 (as illustrated in FIG. 26), for instance a sample pad 102a, the lid 103 may partially cover the fluidic substrate 101, allowing a user to access the inlet 109 to deposit a fluid sample.

According to some embodiments, the sensing device 100 may further comprise one or more electrodes which are placed on the micro-fluidic component 102 of the fluidic substrate 101.

These electrodes may be biocompatible electrodes. The electrodes may be electrically connected to the lid 103 and are allowed to interact with a fluid sample in the micro-fluidic component 102 of the sensing device 100 as they may be in direct contact with a fluid sample in the micro-fluidic component 102. While the lid 103 itself may comprise electrodes, it may be advantageous to separate the electrodes from the lid 103 to allow the lid 103 to be smaller which reduces costs.

According to some embodiments, the micro-fluidic component 102 may comprise a capillary pump.

According to some embodiments, the means for providing a fluid sample may be an integrated needle 104, for instance fabricated from silicon, and comprising an inner fluidic channel 105 connected to the micro-fluidic component 102. The needle 104 may be a protruding portion of the fluidic substrate 101 and may be positioned so as to penetrate skin tissue when pressed against that skin tissue.

The fluidic substrate 101 and the needle 104 may be fabricated from a single piece of silicon. This simplifies the fabrication of the sensing device 100, as separate steps to attach a needle 104 to the fluidic substrate 101 are not required. Also, standard CMOS processing techniques may be used to fabricate the needle 104. The needle 104 is a sharp needle which allows skin tissue to be penetrated. The fluidic substrate 101 and the needle 104 may be both 15 fabricated from silicon. The strength of the silicon allows the needle 104 to be very sharp which eases the penetration of the needle 104 in skin tissue. Further, the strength of the silicon allows skin tissue to be firmly pressed against the needle 104, allowing penetration of skin tissue without bending or breaking the needle 104.

According to some embodiments, the needle 104 may be positioned in a horizontal plane of the fluidic substrate 101 wherein the needle 104 is positioned on a sidewall of the fluidic substrate 101. The needle 104 may be a protruding portion of a sidewall of the fluidic substrate 101. According to a different embodiment, the needle 104 may be positioned on a horizontal plane of the fluidic substrate 101 wherein the needle is positioned perpendicular on a major surface of the fluidic substrate 101. According to some embodiments, the needle 104 may feature an open channel connected to the micro-fluidic component 102, wherein, in use, the skin tissue functions as a sidewall of the needle 104 when skin tissue is penetrated.

The sensing device 100 may be used by pressing skin tissue of a user against the needle 104. When sufficient force is used, the needle 104 penetrates the skin tissue, allowing blood to enter the inner fluidic channel 105 of the needle 104. The needle 104 comprises a tip which is open to allow a fluid sample to enter the inner fluidic channel 105.

When the needle is sharp with a small outer diameter (possibly smaller than 200 um) the penetration of the skin tissue will not cause any discomfort to the user. As the inner fluidic channel 105 of the needle 104 is connected to the micro-fluidic component 102 of the fluidic substrate 101, blood may enter the micro-fluidic component 102. Due to capillary force, blood will propagate through the micro-fluidic component 102.

FIG. 1 illustrates an embodiment of the fluidic substrate 101 with an integrated needle 104 (as part of the fluidic substrate 101), the needle having an inner fluidic channel 105 connected to a micro-fluidic component 102. The microfluidic component 102 may comprise: a sample pad 102*a* (=an inlet), a reagent storage 102*b*, a one-time usage hermetic valve 102*c*, a first trigger valve 102*d*, a mixer 102*e*, a delay line 102*f*, a second trigger valve 102*g*, an heater 102*h* and a wick 102*i*. As illustrated in FIG. 1, all fluidic components in the fluidic substrate 101 are open. The lid 103 may function as a cover to close some or all fluidic components.

According to some embodiments, the fluidic substrate 101 may comprise a cutout 106 wherein the needle 104 is positioned in the cut-out 106. The cut-out 106 is a removed part of the fluidic substrate 101 to offer mechanical protection for the needle 104 which resides in the cut-out 106.

Figure 6:
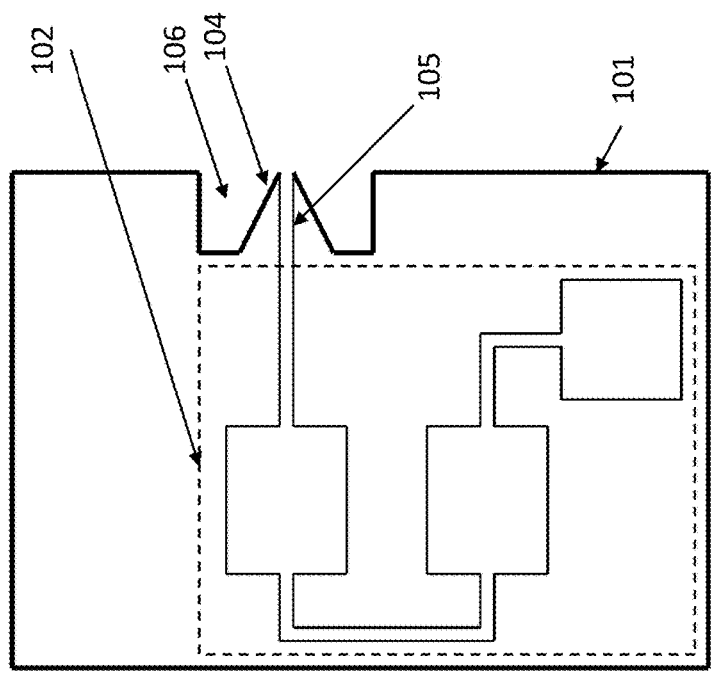
FIG. 6 illustrates a top view of a fluidic substrate featuring a cut-out for a needle, for use in the device of FIG. 5, according to an example embodiment.
Figure 5:
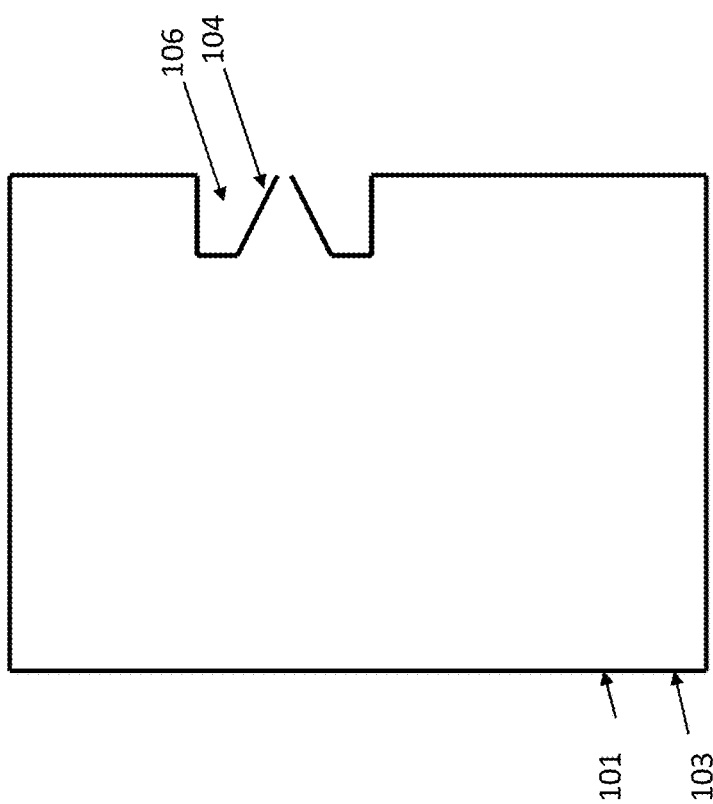
FIG. 5 illustrates a top view of a device for analyzing a fluid sample, featuring a cut-out for a needle, according to an example embodiment.
Figure 7:
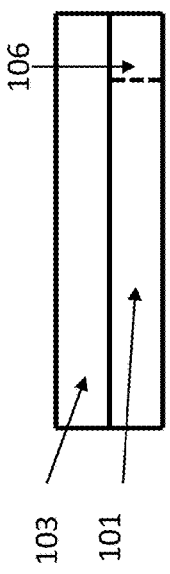
FIG. 7 illustrates a side view of the device of FIG. 5, according to an example embodiment.

FIG. 5 illustrates a top view of an example embodiment wherein the lid 103 is bonded to the fluidic substrate 101. FIG. 6 illustrates a top view of an exemplary fluidic substrate 101, according to an example embodiment. FIG. 7 illustrates a side view of an example embodiment wherein the lid 103 is bonded to the fluidic substrate 101.

As illustrated in FIGS. 5, 6 and 7, the needle 104 is located in a cut-out 106 of the fluidic substrate 101. The cut-out 106 protects the needle 104 from breaking e.g. when the sensing device 100 is inserted in a slot of an external device, e.g. a mobile device such as a smartphone, for instance for readout. The sidewall of the fluidic substrate 101 may feature the cut-out 106. The needle 104 may be positioned in the cut-out 106 to allow a user to penetrate skin tissue when pressed firmly against the cut-out 106. During fabrication, the needle 104 may be fabricated while fabricating the cut-out 106.

As a result, less material is wasted as only the material for the cut-out 106, excluding the material for the needle 104, needs to be removed. The cut-out 106 and needle 104 may be fabricated using standard silicon processing techniques.

According to some embodiments, the fluidic substrate 101 may comprise a protection structure 107 for protecting the needle 104, removably attached to the fluidic substrate 101.

Figure 9:
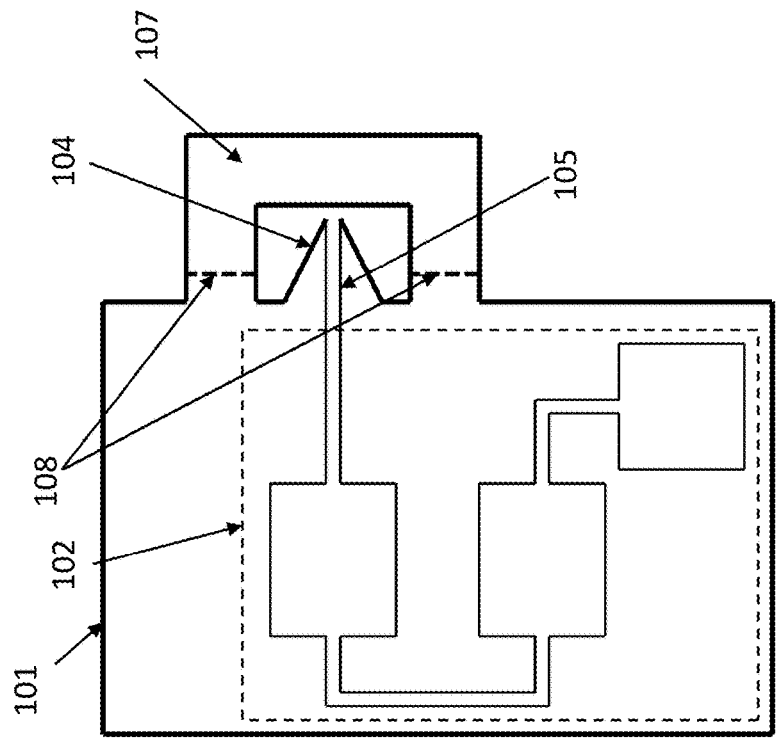
FIG. 9 illustrates a top view of a fluidic substrate featuring a protection structure for a needle, for use in the device of FIG. 8, according to an example embodiment.
Figure 8:
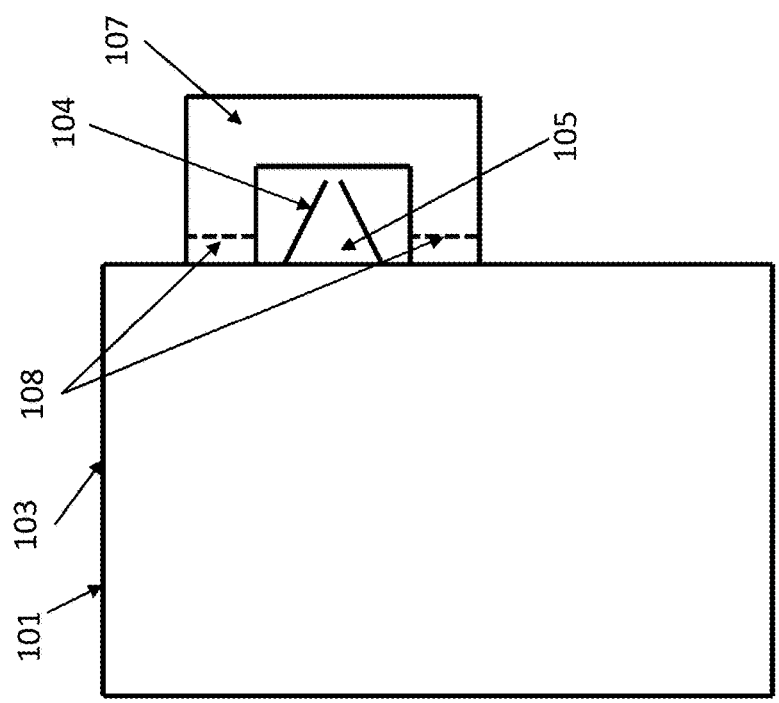
FIG. 8 illustrates a top view of a device for analyzing a fluid sample, featuring a protection structure for a needle, according to an example embodiment.
Figure 10:
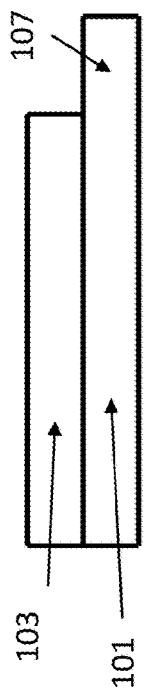
FIG. 10 illustrates a side view of the device of FIG. 8, according to an example embodiment.

According to some embodiments, the protection structure 107 may be attached to the fluidic substrate 101 via at least one anchoring mechanism 108. The protection structure 107 may be detached by breaking the at least one anchoring mechanism 108. The protection structure 107 may be part of the fluidic substrate 101 wherein the anchoring mechanism 108 is a groove in the fluidic substrate 101 to allow breaking of the protection structure 107 at the groove. FIG. 8 is a top view of such an embodiment of a sensing device 100. As can be seen in FIG. 9 (illustrated is a top view of an exemplary embodiment of a fluidic substrate 101 for use in a sensing device 100 according to some embodiments, for instance a sensing device 100 as illustrated in FIG. 8), the protection structure 107 is part of the fluidic substrate 101 and features two anchoring mechanisms 108 which allow detaching of the protection structure 107 from the fluidic substrate 101. FIG. 10 illustrates a side view of the sensing device 100 of FIG. 8.

According to some embodiments, the means for providing a fluid sample is an inlet 109. The inlet 109 may be an indentation in the fluidic substrate 101 which is connected to the microfluidic component 102 by a fluidic channel. To use the sensing device 100, a user may deposit a drop of bodily fluid such as blood or saliva on the inlet 109 of the sensing device 100. Due to capillary force, the bodily fluid will propagate through the micro-fluidic component 102.

FIG. 26 illustrates a de-assembled sensing device 100, comprising a fluidic substrate 101 comprising an inlet 109 and a microfluidic component 102, a lid 103 and an package 110. The package 110 may comprise a base and a top which can be assembled together to package the fluidic substrate 101 and the lid 103, thus protecting these from environmental influences such as dust. The package may comprise a through-hole 260 for depositing a fluid sample on an inlet 109 of the fluidic substrate 101. When all parts are assembled, the sensing device 100 may function as a standalone wireless device for analyzing a fluid sample.

According to some embodiments, at least a part of the lid 103 may be in contact with the fluid sample when the fluid sample is present in the sensing device 100. As the lid 103 is a CMOS chip, electronic circuitry present on a surface of the chip may be in direct contact with the fluid sample when the lid 103 is functioning as a side-wall of an open microfluidic component 102 in the fluidic substrate 101. In this case, the side of the chip comprising electronic circuitry may be bonded to an open micro-fluidic component 102 of the fluidic substrate 101 wherein the electronic circuitry is aligned with parts of the micro-fluidic component 102 where interaction with a fluid sample is desired. This may improve the interaction between the electronic circuitry and the fluid sample.

According to some embodiments, the lid 103 may comprise bonding layers to enable bonding of the lid 103 to the fluidic substrate 101.

According to some embodiments, a first side of the fluidic substrate 101 comprising an open micro-fluidic component 102 may be bonded to a first side of the CMOS chip 103 comprising at least one electrical component.

According to an embodiment, the lid 103 comprises a transistor layer, the transistor layer being electrically connected at least one electrical component, the electrical component being at least one of the following: biosensing circuitry, electrodes for sensing purposes, electrodes for fluid manipulation purposes, circuitry for data communication purposes, circuitry for wireless data communication purposes, temperature sensors, heater electrodes for temperature control or temperature cycling and fluid sensors and electrodes for fluidic viscosity control. The circuitry for wireless data communication may comprise provisions for communication via a Bluetooth radio or a WiFi module for wirelessly transmitting data from electronic circuitry in the lid 103. The sensing device 100 may communicate with an external device such as a mobile device which may be used to further process the data.

The lid 103 is a CMOS chip. According to some embodiments, the CMOS chip comprises a silicon substrate 111, a transistor layer 112, at least one electrical component electrically connected to the transistor layer 112 and at least one bonding layer 115. The at least one electrical component may be biosensing circuitry, electrodes for sensing purposes, electrodes for fluid manipulation purposes, circuitry for data communication purposes, circuitry for wireless data communication purposes, temperature sensors, heater electrodes for temperature control and fluid sensors and electrodes for fluidic viscosity control.

Figure 18:
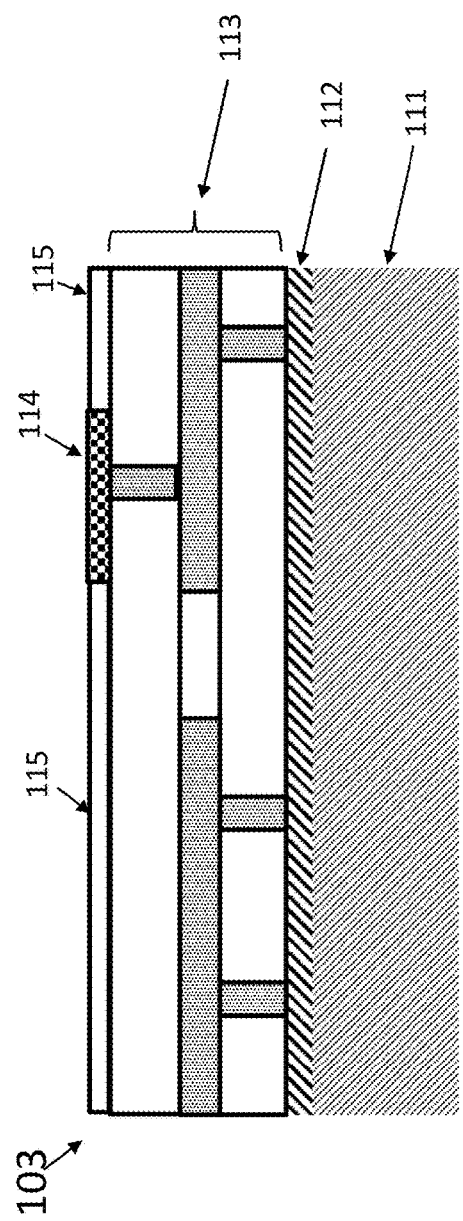
FIG. 18 illustrates a CMOS chip for use in a device, according to an example embodiment.

A particular embodiment of a lid 103 is illustrated in FIG. 18. In this embodiment, the CMOS chip 103 comprises a silicon substrate 111. Atop the silicon substrate 111 a transistor layer 112 may be present. Atop the transistor layer 112 an interconnection layer 113 may be present. Atop the transistor layer 112, at least one electrical component may be present electrically connected to the transistor layer 112 via the interconnection layer 113. The interconnection layer 113 may comprise a plurality of metal layers. According to some embodiments, atop the transistor layer 112, a bonding layer 115 and at least one electrode 114 may be present. The electrode 114 may be electrically connected to the transistor layer via the interconnection layer 113.

According to some embodiments, the at least one electrical component may be a biocompatible electrode which is fluid corrosion free and chemically inert. According to a specific embodiment, the at least one electrode 114 is TiN electrode.

According to some embodiments the bonding layer 115 may be a layer which allows bonding of the CMOS chip 103 to the fluidic substrate 101 at low temperatures and voltages. These conditions do not damage the CMOS chip, neither do they damage reagents or for instance proteins which may be provided on the microfluidic substrate 101. According to a specific embodiment, the bonding layer 115 may be a SiO2 or polymer layer.

Figure 19:
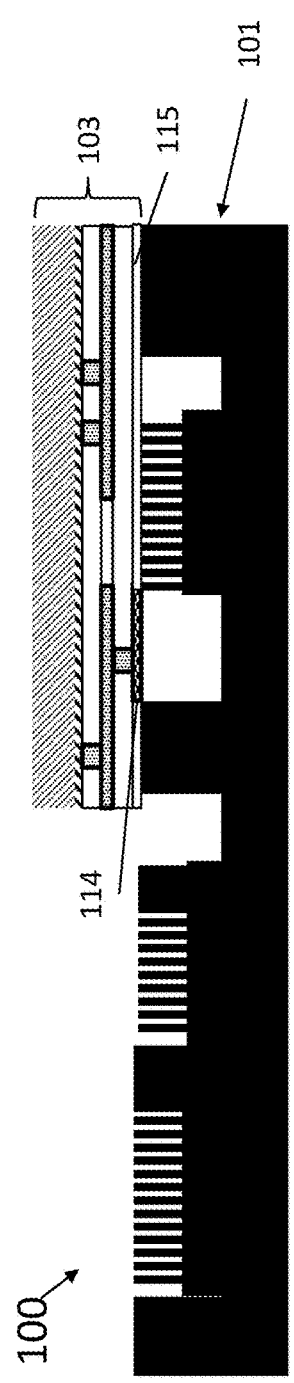
FIG. 19 illustrates the bonding of a CMOS chip with a fluidic substrate, according to an example embodiment.

FIG. 19 illustrates a sensing device 100, wherein a CMOS chip 103 as illustrated in FIG. 18 is bonded to a fluidic substrate 101. The side of the CMOS chip 103 comprising the bonding layer 115 and the electrode 114 is bonded to the side of the fluidic substrate 101 comprising an open microfluidic component 102. This means that the CMOS chip 103 as illustrated in FIG. 18 is flipped upside down with respect to its position as illustrated in FIG. 18.

The electrode 114 is thereby in direct contact with a fluid sample present in the micro-fluidic component 102. The bonding layer 115 is used to attach the CMOS chip 103 to the fluidic substrate 101.

Figure 20:
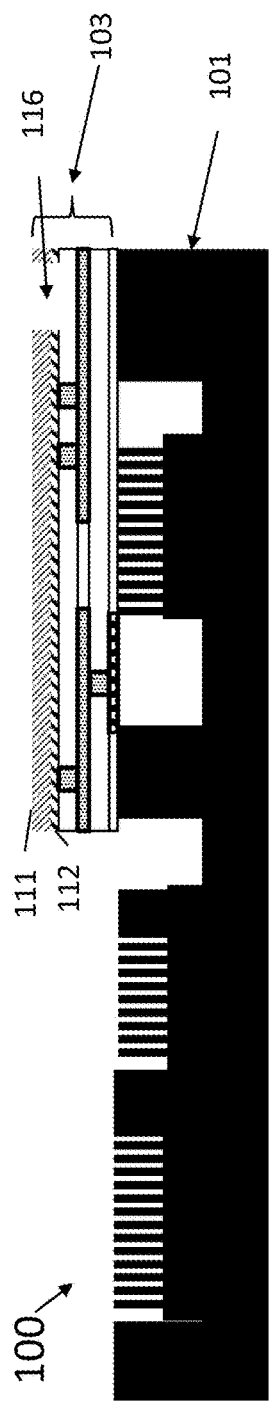
FIG. 20 illustrates the bonding of a CMOS chip with a fluidic substrate, wherein the CMOS chip comprises a silicon I/O interconnect, according to an example embodiment.

According to some embodiments, the CMOS chip 103 may comprise at least one silicon I/O connection 116, as illustrated in FIG. 20. The silicon I/O connection 116 may be a backside opening through the substrate 111 to access electrical signals of the CMOS chip 103 in the transistor layer 112. Further, in yet alternative embodiments, the silicon I/O connection 116 may be a backside opening through both the substrate 111 and the transistor layer 112 to access electrical signals of the CMOS chip 103 in the interconnection layer 113. FIG. 20 illustrates the sensing device 100 wherein a CMOS chip 103 is bonded to a fluidic substrate 101 and wherein the CMOS chip 103 features a silicon I/O connection 116 through both the substrate 111 and the transistor layer 112.

According to some embodiments, the fluidic substrate may comprise an open micro-fluidic component 102 and the fluidic substrate may be covered partly by the CMOS chip 103. Part of the micro-fluidic component 102 is not covered, which allows reagents to be applied/spotted on specific open parts of the micro-fluidic component 102. In this case, no extra through holes are needed to apply reagents after bonding of the fluidic substrate 101 to the CMOS chip 103. It is also beneficial that the CMOS chip area is smaller, as the active electronics are the more expensive part of the disposable.

According to some embodiments, the CMOS chip 103 may further comprise at least one I/O pad 117. The at least one I/O pad 117 may be located on the interconnection layer 113.

Figure 21:
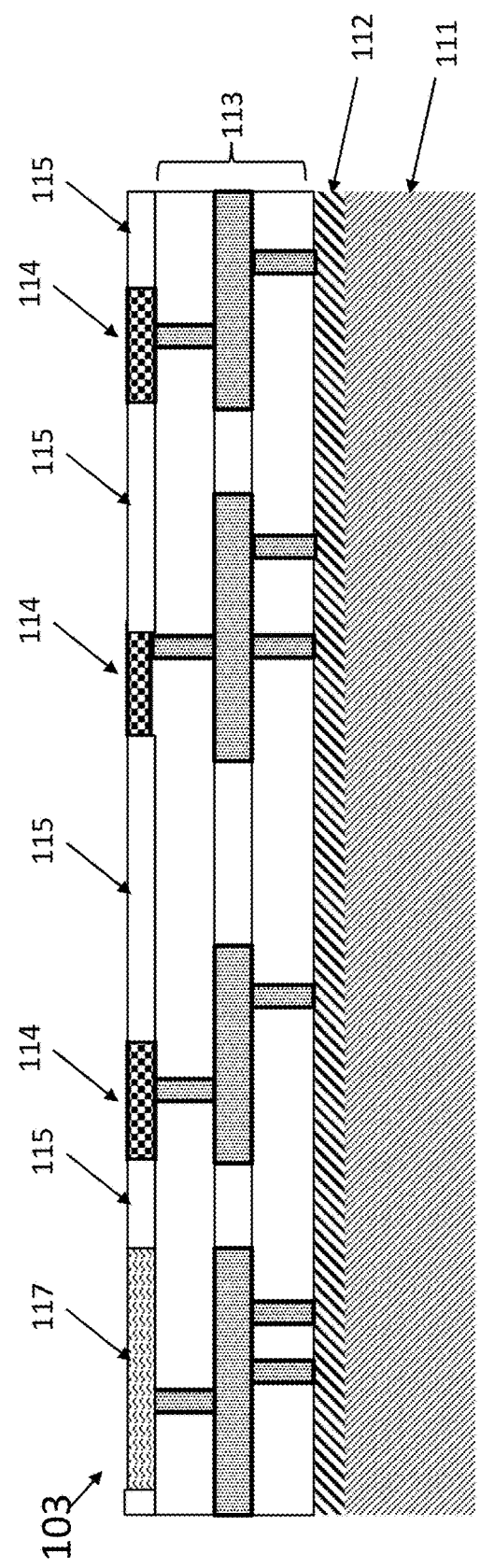
FIG. 21 illustrates a CMOS chip, the CMOS chip comprising an I/O pad, according to an example embodiment.

FIG. 21 illustrates an embodiment of a CMOS chip 103. The CMOS chip 103 comprises a silicon substrate 111. Atop the silicon substrate a transistor layer 112 is present. Atop the transistor layer 112, an interconnection layer 113 is present. The interconnection layer 113 may comprise a plurality of metal layers to interconnect the transistor layer 112 with electrical components. Atop the transistor layer 112, a bonding layer 115, an I/O pad 117 and, in the embodiment illustrated, a plurality of electrodes 114 are present. The electrodes 114 are electrically connected to the transistor layer 112 via the interconnection layer 113. The I/O pad 117 is also electrically connected to the transistor layer 112 via the interconnection layer 113.

According to some embodiments, a first part of a first major surface of the CMOS chip 103 may cover the fluidic substrate 101, a second part of the first major surface of the CMOS chip 103 may not cover the fluidic substrate 101. In these embodiments, the CMOS chip 103 may either be larger than the fluidic substrate 101, or it may be laterally shifted with respect to the fluidic substrate 101 so that a portion of the CMOS chip 103 forms an overhang with respect to the fluidic substrate 101.

The second part of the first major surface of the CMOS chip 103 may comprise at least one I/O pad 117 to have access to the I/O pad 117.

Figure 22:
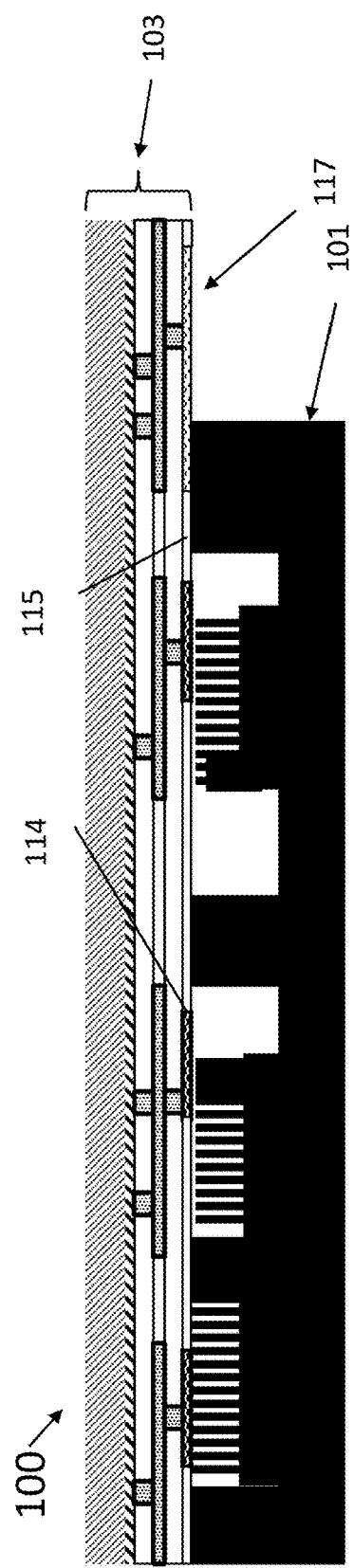
FIG. 22 illustrates a CMOS chip for use in a device, the CMOS chip comprising an I/O pad bonded to a fluidic substrate, wherein a part of the CMOS chip overlaps the fluidic substrate, according to an example embodiment.

FIG. 22 illustrates a CMOS chip 103 as illustrated in FIG. 21, bonded to a fluidic substrate 101. A first part of the CMOS chip 103 at least partly, and in the embodiment illustrated fully covers the fluidic substrate 101 wherein electrodes 114 are in direct contact with a fluid sample when present in the microfluidic component 102 of the sensing device 100. The bonding layers 115 are used to bond a first part of the CMOS chip 103 to the fluidic substrate 101. A second part of the CMOS chip 103 forms an overhang which does not cover the fluidic substrate 101. The second part comprises the I/O pad 117. This overhang allows easy access to the I/O pad 117. This allows standard I/O pad dimensions and packaging approaches to be used for inserting the substrate in slots typically used for smartcards. Additional processing steps to fabricate silicon I/O connections (e.g. a hole through the substrate and transistor layer) to access electrical signals in the CMOS chip 103 are not required.

According to some embodiments, the fluidic substrate 101 further comprises at least one optical waveguide to allow optical excitation and sensing of the fluid sample when present in the sensing device 100.

According to some embodiments, the fluidic substrate 101 or the lid 103 comprises at least one through-hole for application of a biochemical reagent to a region of the microfluidic component 102 or to a region of the lid 103. The through-holes in the fluidic substrate 101 or the lid 103 allow the application of biochemical reagents to specific regions of the micro-fluidic component 102 or to specific regions of the lid 103. This is reagents to be applied after attachment of the lid 103 to the fluidic substrate 101.

Figure 23:
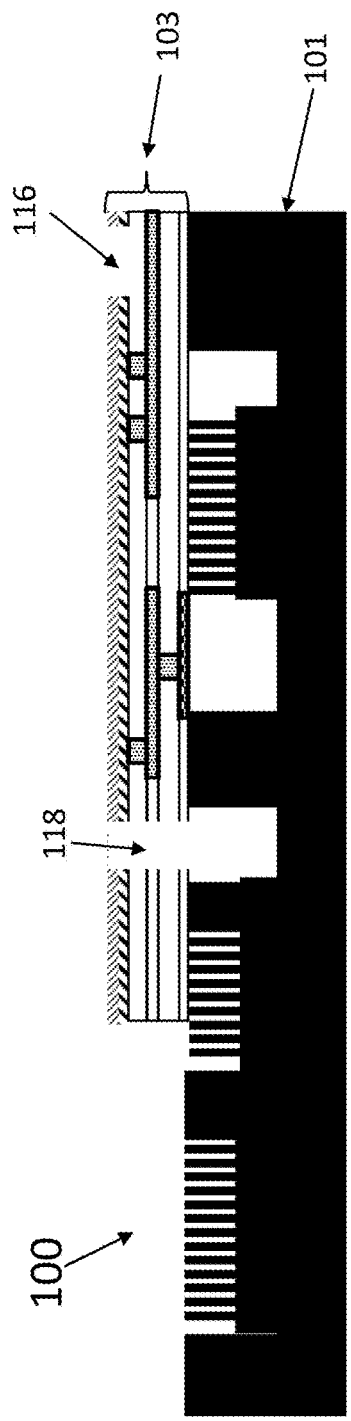
FIG. 23 illustrates the bonding of a CMOS chip with a fluidic substrate, wherein the CMOS chip comprises a through hole, according to an example embodiment.

According to some embodiments, the CMOS chip 103 may comprise at least one through-hole 118. When attached to the fluidic substrate 101, the through hole 118 in the CMOS chip 103 allows reagent spotting on a specific location of the micro-fluidic component 102 in the fluidic substrate 101 or on a specific part of the CMOS chip 103. FIG. 23 illustrates such an embodiment wherein the CMOS chip 103 comprises one through-hole 118. In this embodiment, the CMOS chip further comprises a silicon I/O connection 116. As illustrated, the CMOS chip 103 completely covers a part of the fluidic substrate 101.

Figure 24:
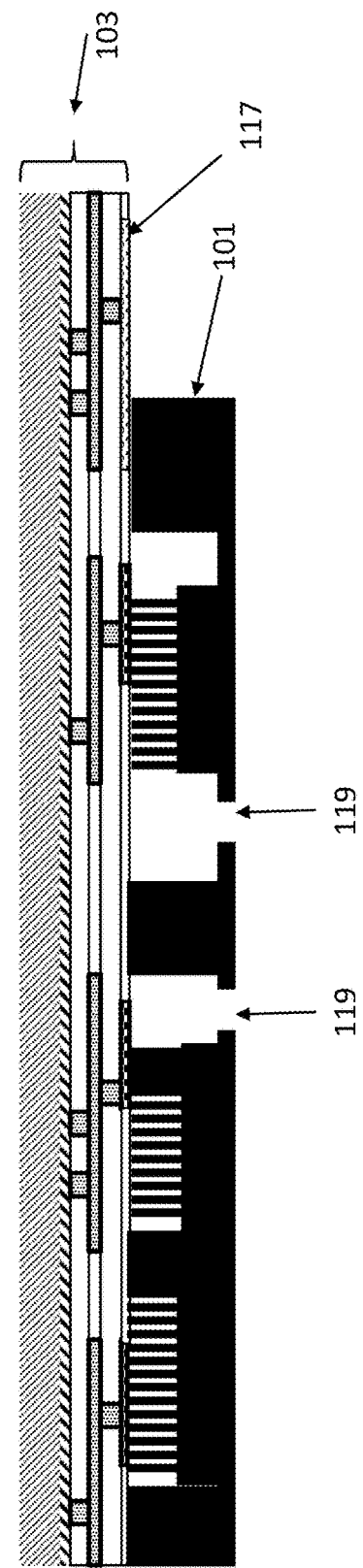
FIG. 24 illustrates the bonding of a CMOS chip with a fluidic substrate, wherein the fluidic substrate comprises two through holes, according to an example embodiment.

According to same or alternative embodiments, a first side of the fluidic substrate 101 comprises the open micro-fluidic component 102. The other side, opposite to the side where the micro-fluidic component 102 is provided, may comprise a at least one through hole 119. The through hole 119 allows reagent spotting on a specific location of the micro-fluidic component 102 in the fluidic substrate 101 or on a specific part of the CMOS chip 103. FIG. 24 illustrates such an embodiment wherein the fluidic substrate comprises two through holes 119. A part of the CMOS chip 103 covers the fluidic substrate 101, the part not covering the fluidic substrate 101 but forming an overhang comprises an I/O pad 117.

According to some embodiments, the lid 103 may be bonded to the fluidic substrate 101 using a polymer, which may be a lithographically patterned polymer. The material for forming the bonding between the lid 103 and the fluidic substrate 101 should be suitable for perform a Si—Si bonding, which may be at low temperature, for instance room temperature. This is compatible with CMOS circuits being present on the lid 103 and which should not be destroyed by the bonding process, and with reagents being present on or in the fluidic substrate 101, and which should also not be destroyed by the bonding process. Suitable bonding materials for bonding the lid 103 to the fluidic substrate 101 are for instance photopatternable PDMS, obtainable from Dow Corning; SU8, obtainable from Micr Chem; or OSTE, obtainable from Mercene Labs. These bonding materials all have room temperature as bonding temperature.

According to another example embodiment, the lid 103 is bonded to fluidic substrate 101 using a CMOS compatible packaging technique. The use of CMOS packaging techniques may be used when the fluidic substrate 101 is a silicon substrate and the lid 103 is a CMOS chip.

According to some embodiments, the sensing device 100 may further comprise metal contacts electrically connected to the lid 103 for read-out of electrical signals from the lid 103. The metal contacts may be located on the lid 103, electrically connected to electronic circuitry in the lid 103.

The position and shape of the metal contacts may be selected according to standards, allowing insertion of the sensing device 100 in standardized slots such as slots for memory cards (e.g. CompactFlash, SmartMedia, MultiMedia Card or Secure Digital (SD) memory cards) commonly used in communication devices such as mobile devices. The insertion of the sensing device 100 in a mobile device allows processing of the electrical signals from the lid 103 by a processor and/or other electronic components present in the mobile device. For example, a processor of a smartphone may be used to process electrical signals and/or to display data.

According to some embodiments, at least a part of the fluidic substrate 101 and/or the lid 103 may be fabricated from a transparent material to allow optical inspection of a fluid sample when the fluid sample is present in the microfluidic component 102. The part of the fluidic substrate 101 that is fabricated from a transparent material may be part of the micro-fluidic component 102 of the sensing device 100. The transparent part may be a side-wall of the micro-fluidic component 102 of the sensing device 100. The transparent material allows optical inspection of a fluid sample in the sensing device 100. An optical detector may be used to optically inspect a fluid sample, in order for instance to detect an analyte. The optical detector may be an image sensor which may be part of an external device or may be integrated in the sensing device 100. The transparent material may be a transparent oxide or polymer. For microscopy purposes, a part of the lid 103 or a part of the fluidic substrate 101 may be transparent. For lens-free imaging purposes, a part of the lid 103 and a part of the fluidic substrate 101 may be transparent to enable working in transmission mode wherein a radiation source may be used to radiate an object in a fluid sample in the sensing device 100 through the transparent part of the lid 103 and a detector may be used to detect signals from the radiated object through the transparent part of the fluidic substrate 101. The signals may be diffraction patterns of a radiated object in the fluid sample.

Figure 33:
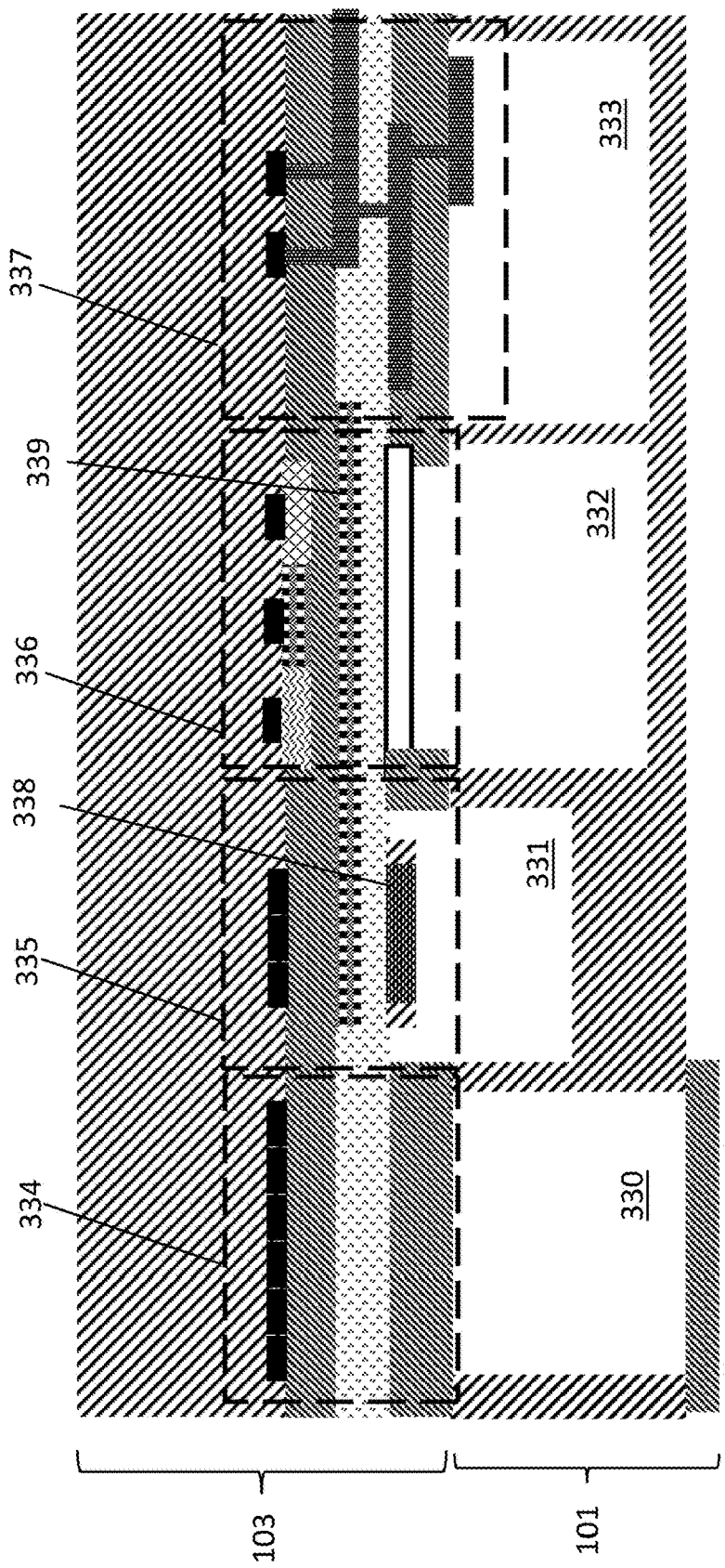
FIG. 33 is a cross-sectional view of a device, wherein a plurality of functionalities are supported by a single CMOS technology, according to an example embodiment.

FIG. 33 illustrates a sensing device 100, where a fluidic substrate 101 and a lid 103 are bonded to one another. The fluidic substrate 101 comprises different microfluidic components for multi-omic analysis, in the embodiment illustrated comprising a plurality of chambers 330, 331, 332, 333 and microfluidic channels (not illustrated). The chambers may have different depths, depending on their function and the type of measurement being performed. The chambers may be separated by valves that may be actuated in any suitable way, for instance by fluidic forces or by electricity. Electrodes for actuation may be provided on the fluidic substrate 101 or on the lid 103. The CMOS chip forming the lid 103 may thus incorporate different functionalities, such as for instance a CMOS microscopic imager 334, CMOS optical detectors 335, 336 and CMOS electrical circuitry 337 for heating and/or sensing. The CMOS microscopic imager 334 may comprise CMOS active pixels for readout of optical signals from the fluid sample in the microfluidic component 102. The CMOS optical detector 335 comprises an optical resonator 338. A waveguide 339 may be present for transporting measurement light from one location of the CMOS chip 103 to another location. The waveguide may for instance be used for irradiating the sample for performing lensfree microscopy. Furthermore, filters may be provided in the fluidic substrate 101 or in the lid 103 for rejecting optical excitation from emission, so as to enable measurement of a fluorescent signal. Also multispectral filters may be provided in the fluidic substrate 101 or in the lid, for measurement fluorescent signals with multiple colours.

This way, detection of different types of markers can be performed within a single, disposable, detection device.

According to some embodiments, the shape of the sensing device 100 allows insertion into a mobile communication device. According to some embodiments, the sensing device 100 has the shape/dimensions of a memory card. The dimensions of the sensing device 100 may be according to standards, e.g. according to standards of memory cards used in mobile devices such as: CompactFlash, SmartMedia, MultiMedia Card, Secure Digital memory cards or any other type.

Figure 31:
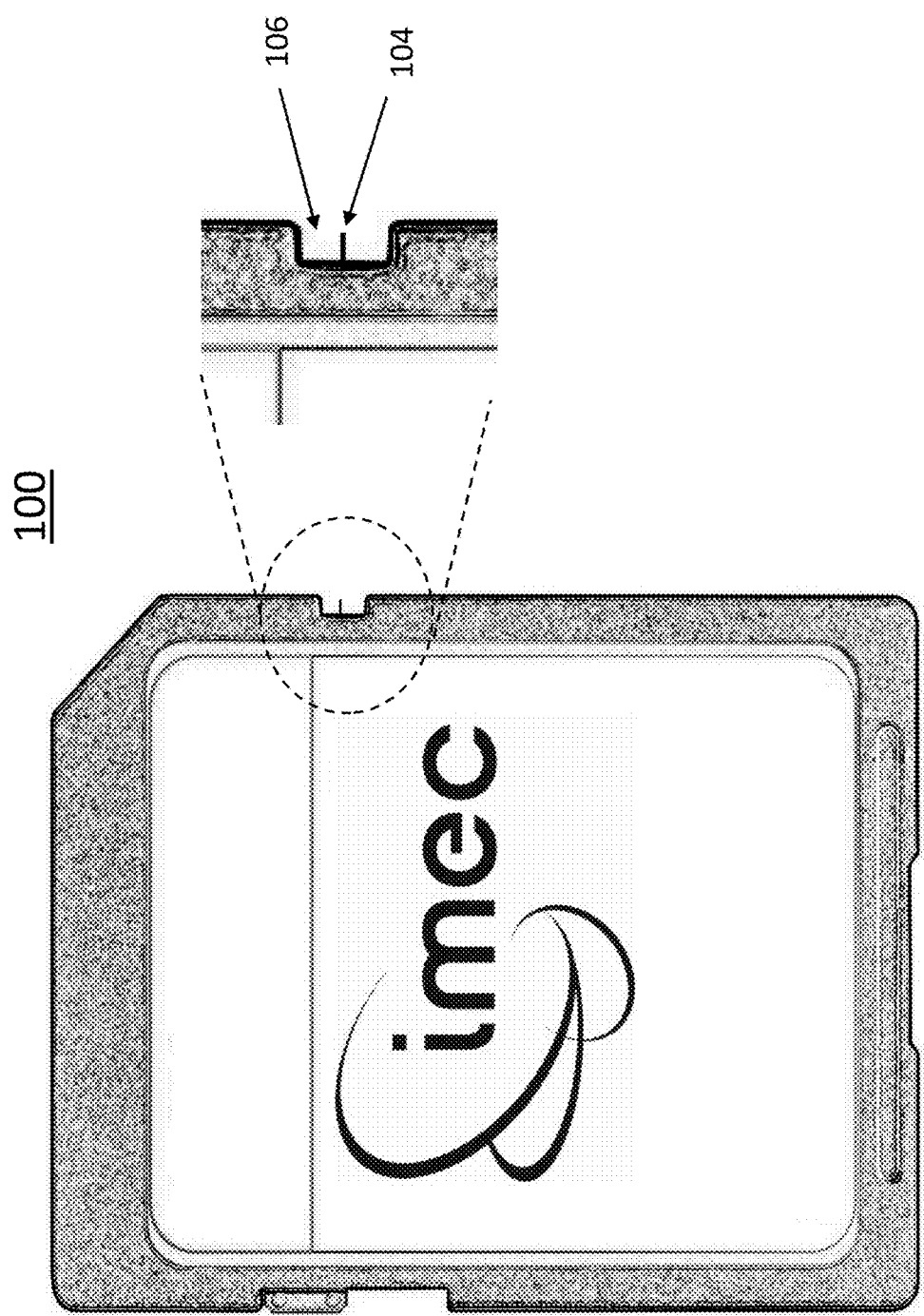
FIG. 31 illustrates a device in the shape of an SD card, according to an example embodiment.
Figure 32:
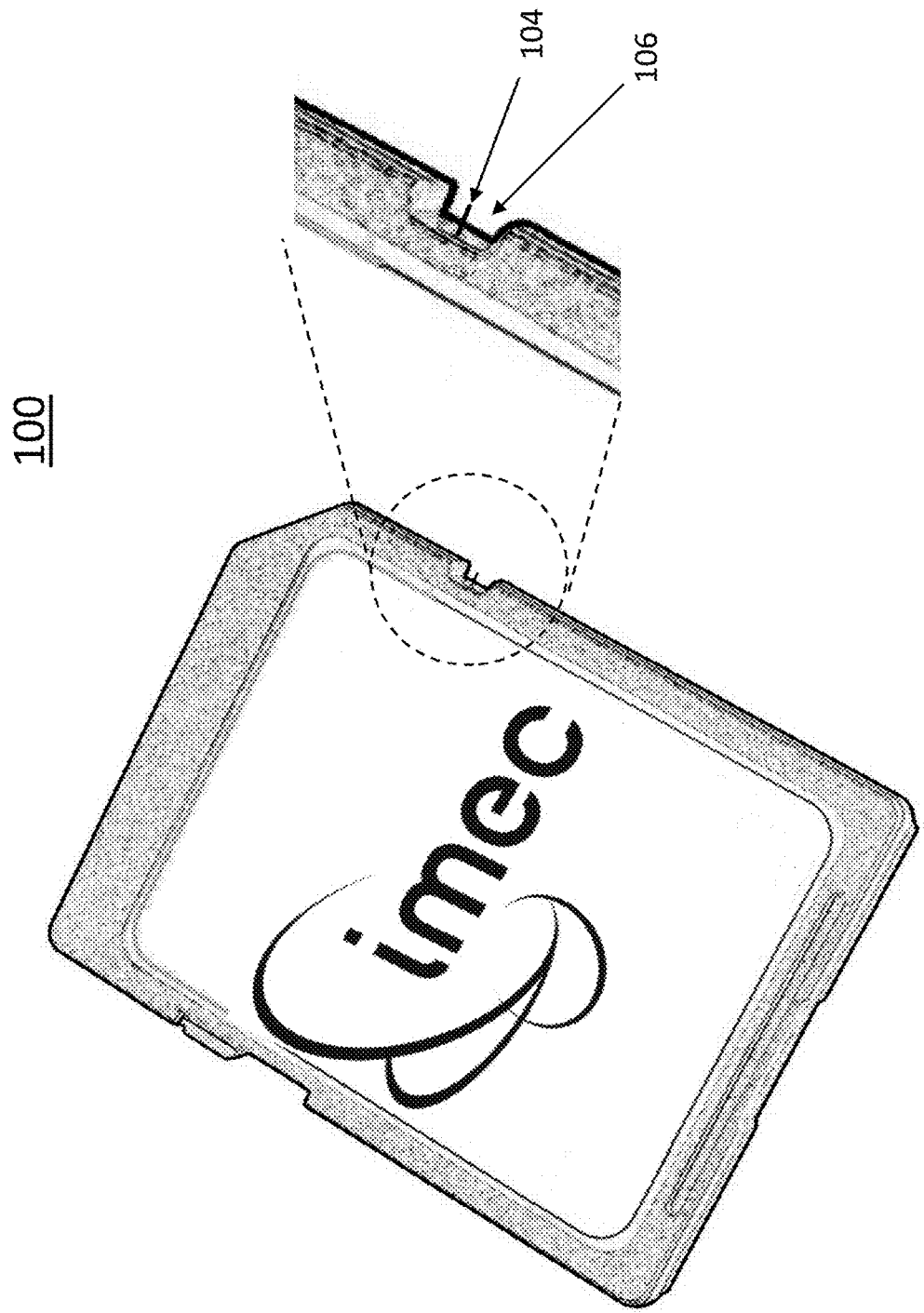
FIG. 32 illustrates a device in the shape of an SD card, according to an example embodiment.

FIGS. 31 and 32 illustrate an embodiment wherein the sensing device 100 has the shape of an SD card. Inside the cut-out 106 (which is always present according to SD card standards), a needle 104 is present. At the other side of the SD card, the metal contacts are present and electrically connected to the lid 103 to allow read-out of electrical signals from the lid 103 which may be further processed by the device in which the SD card is inserted.

According to some embodiments, the lid 103 or the fluidic substrate 101 may further comprise a compartment for powering the sensing device 100, such as a battery compartment (not illustrated) which is electrically connected to the lid 103.

In another aspect, some embodiments relate to a method to fabricate a sensing device 100 as disclosed earlier. The method comprises: providing a fluidic substrate 101; providing a lid 103; attaching the fluidic substrate 101 to the lid 103 to close the fluidic substrate 101 at least partly; characterized in that: the fluidic substrate 101 is a silicon fluidic substrate and the lid 103 is CMOS chip; and wherein the fluidic substrate 101 is attached to the lid 103 using a CMOS compatible bonding process.

The fluidic substrate 101 is bonded to the lid 103 using a CMOS compatible bonding process. In conventional devices, bonding is performed using high temperature/voltage bonding techniques. These bonding techniques may damage electronic circuitry present in the CMOS chip and/or reagents present in the microfluidic substrate 101. The use of a CMOS compatible bonding enables bonding at lower temperatures/voltages and therefore preserves the electronic circuitry of the lid 103 and the reagents present in the microfluidic substrate 101. According to some embodiments, the bonding may be performed via a wafer to wafer or die to wafer bonding process such as direct oxide to oxide bonding or bonding via a pattern-able polymer. Additionally, the bonding may be performed at a low temperature in case some reagents are already spotted on one of the substrates during the fabrication flow.

The fluidic substrate 101 may be fabricated using a combination of coarse and fine structures in a single piece of silicon substrate by a combination of two hard masks, protection and de-protection of layers, etching of coarse and etching of fine structures. The fine structures may be structures configured to enable a controlled capillary suction in the micro-fluidic component 102 of the sensing device 100. The fine structures may comprise micro-pillars 270 and/or other microstructures. The coarse structures may be structures for storing larger volumes of fluids e.g. reagent storage 102b for storing reagents, or a wick 102i. Using silicon may be beneficial since the very high anisotropic etching of silicon results in fine structures with extremely high aspect ratios. The silicon micro-pillars 270 typically have lateral dimensions from 1 um to 20 um with aspect ratios of 20-50. High aspect ratios in having allow for a high surface to volume ratio, which is essential for capillary flow. The high aspect ratio fine structures, combined with the coarse structures allow to implement more complex capillary fluidic functions in a more compact footprint than is achievable with any other material. More complex functions include separation (e.g. cells from molecules), mixing, valving, thermally controlled reactions . . . . Moreover, silicon is an inert material, which assists with biochemical reactions. The One advantage of the compact fully integrated disposable sensing device 100 results from the use of silicon for both the fluidic substrate and the CMOS lid. The reduced footprint also results in reduced cost of the entire sensing device.

According to some embodiments, providing a fluidic substrate 101 comprises providing a silicon substrate 201, illustrated in FIG. 11, and patterning the silicon substrate to form a micro-fluidic component 102 and a means for providing a fluid sample in the sensing device 100, the micro-fluidic component 102 being configured to propagate a fluid sample via capillary force through the sensing device 100.

According to some embodiments, providing a fluidic substrate 101 comprises: providing a silicon substrate 201, providing an oxide mask 202, patterning the oxide mask 202 by using a first patternable mask layer 210, so as to create fine structures 203 in the oxide mask 202 (FIG. 12); providing a protection layer 204 to protect the patterned oxide mask; patterning coarse structures in a second patternable mask layer 211 (FIG. 13); etching of the coarse structures 205 in the silicon substrate 201 through the second mask layer 211 (FIG. 14); removing the second mask layer 211 and growing oxide 206 (FIG. 15) for protecting the coarse structures 205; removing the protection layer 204 (FIG. 16) and etching the fine structures 203 using the oxide layer 206 as an etch mask (FIG. 16); removing the oxide 206 (FIG. 17). The resulting structure is a microfluidic substrate 101 which may be used in a sensing device 100.

FIGS. 11-17 illustrate how the fluidic substrate 101 may be fabricated. According to some embodiments, the fluidic substrate 101 may be fabricated by performing:

Patterning fine structures 203 comprising: providing a silicon substrate 201, providing an oxide mask 202, patterning the oxide mask 202 to create fine structures 203 in the oxide mask 202;

providing a protection layer 204 to protect the oxide 202;

performing lithography of coarse structures 205;

performing etching of the coarse structures 205;

growing oxide 206 for protecting the coarse structures 205 wherein the protection layer 204 on the fine structures 203 prevents oxide growth;

removing the protection layer 204 and etch the fine structures 203;

removing the oxide 206.

According to some embodiments, the protection layer 204 may be a nitride layer.

According to some embodiments, providing the CMOS chip 103 comprises: providing a silicon substrate 111, fabricating a transistor layer 112 atop the silicon substrate and providing an interconnection layer 113 atop the transistor layer. The interconnection layer may comprise at least one metal layer. The CMOS chip 103 is fabricated using standard CMOS process techniques.

Further, on top of standard CMOS process flows, additional components may be deposited or patterned on the interconnection layer 113 such as biocompatible electrodes, a bonding layer, I/O pads or other components.

According to some embodiments, through holes 109, 118 may be etched through the fluidic substrate 101 or the CMOS chip 103 to enable fluidic access for applying of reagents to the fluidic substrate 101 or CMOS chip 103. The through-holes in the CMOS chip 103 may be fabricated whilst fabricating silicon I/O interconnections 116 in the CMOS chip 103. The through-holes in the fluidic substrate 101 may be fabricated by first thinning the fluidic substrate 101 and then etching the throughholes.

According to some embodiments, the CMOS chip 103 may 5 be bonded to the fluidic substrate 101 using a die to wafer or wafer to wafer bonding process.

To access electrical signals of the CMOS chip 103, silicon I/O contacts 116 may be provided.

According to some embodiments, the contacts may be fabricated by thinning the silicon substrate 111 of the CMOS chip 103 and performing a back side etching on the silicon substrate 111 to gain access to a metal layer of the interconnection layer 113.

Alternatively, a CMOS chip 103 comprising an I/O pad 117 at a first side of the chip 103 may be provided, wherein the first side of the CMOS chip 103 is bonded to the fluidic substrate 101 and wherein the first side of the CMOS chip 103 comprising the I/O pad 117 does not cover the fluidic substrate 101.

This is for example illustrated in FIG. 22. The I/O pad 117 is accessible when the CMOS chip 103 is bonded to the fluidic substrate 101. The I/O pad 117 may be used as a metal contact on a memory card.

According to some embodiments, the CMOS chip 103 is bonded to the fluidic substrate 101 while aligning at least one electrical component on a first side of a CMOS chip 103 with the micro-fluidic component 102. For example, sensing and actuating electrodes on the first side of the CMOS chip 103 are aligned with a sensing or actuation side in the fluidic substrate 101. This allows direct contact of a fluid sample with electrical components present on the CMOS chip 103 when a fluid sample is present in the sensing device 100.

According to some embodiments, surfaces of the fluidic substrate 101 and the lid 103 are partially or fully coated to modify surface interactions with the fluid sample. The surfaces may be inner surfaces of the micro-fluidic component 102 or a surface of the CMOS chip 103 that is bonded to the fluidic substrate 101. In particular those parts of the surface of the CMOS chip 103 that are in contact with a fluid sample present in the micro-fluidic component 102. The coating may be a hydrophilic coating.

The surfaces of the micro-fluidic component 102 and/or the side of the CMOS chip 103 bonded to the fluidic substrate 101 can be made hydrophilic in order to improve the wetting behavior of the surfaces, thereby promoting capillary flow. The surfaces can also be treated in order to avoid absorption or adhesion of biomolecules on the walls. The coating can be done for example by vapor coating with silanes.

According to some embodiments the coating may be performed locally on certain parts of the fluidic substrate 101 (e.g. in some micro-fluidic channels) or on certain parts of the CMOS chip 103.

According to some embodiments, at least one throughhole is fabricated in the fluidic substrate 101 by first etching the through-hole and then filling the through-holes with a transparent oxide of polymer.

Some embodiments improve the functionality, portability and manufacturability of compact disposable point of care devices. An example embodiment is a fully integrated silicon device with a needle or an inlet for the intake of blood or any other body fluid. The sensing device features a capillary fluidic system for the propagation of a fluid sample through the sensing device via capillary action. A capillary pump functioning as the wicking zone of the capillary fluidic system may be used to propagate the fluid sample in the sensing device. A sensor chip reading out signals produced by biochemical sensing reactions inside the capillary system may be used to add biosensing functionality to the sensing device. Further, the sensing device features a data communication interface for sending data to a personal computer, a computing unit, smartphone or any other wireless communication device. The sensing device may function as a stand-alone system wherein a power interface such as a battery powers electronic circuitry such as a micro-chip in the sensing device.

Alternatively, the sensing device may be powered via a communication port of the sensing device.

The sensing device may further comprise fluidic manipulation structures including filtering, mixing, valves structures. A protection structure with a cut off zone to protect and prevent breaking the needle before usage may be present to avoiding contamination before usage. Structures such as electrically controllable fluidic manipulation structures including electrowetting, electro and dielectrophoretic manipulation may be present to interact with a fluid sample in the sensing device. Electronic controllable heaters may be present for accurately controlling the temperature of the chip or for thermal cycling purposes.

Another example embodiment includes an elegant, low cost and compact manner to fabricate all of the above functions by providing a silicon substrate which may comprise lithographically defined channels, micro pillars and microstructures of various shapes fabricated by deep Reactive Ion Etching and designed to function as a capillary fluidic platform. The silicon substrate may have a provision for making a needle and a cut off zone for protecting the needle. The silicon substrate can have different etch depths allowing for precise control over the volume and capillary flow of a fluid sample in the sensing device. The silicon substrate may be closed by a CMOS substrate (e.g., lid 103) comprising CMOS electronics containing a transistor layer.

The electronics may be designed to provide functionality including sensing, actuating, signaling, data processing and data communication and therefore replaces the point of care instrument. Some of the electrodes may be in direct contact with the fluid, these electrode may be protected in a fluid compatible manner. The silicon substrate may be closed by the CMOS substrate by bonding both substrates in a leakage free and biocompatible manner. This can be done via a wafer to wafer or die to wafer bonding process such as bonding via a patternable polymer.

The inner silicon substrate surfaces which may be in contact with the body fluids may feature a hydrophilic layer via coating of the inner channels. Additionally, through wafer holes may be fabricated in the silicon substrate for supplying reagents after the sensing device has been bonded. For each analysis, different reagents can be supplied. The same sensing device becomes configurable for different diseases by simply adding reagents through the through-holes in the last production step. The sensing device may be manufactured using CMOS compatible processing steps which lower production cost and enable the sensing device to be used as disposable device.

Further, the sensing device may comprise components to enable interfacing with standard user interfaces. For example, the use of such a sensing device as a smartcard in wireless communication devices inserted in slots typically foreseen for smartcards. For example, the use of such a sensing device together with a compact and cheap battery and low cost communication device (e.g. Bluetooth, NFC). For example, the use of such a sensing device together with a wired communication interface (e.g. USB)

Some embodiments may be used to detect DNA/RNA from body fluids and perform an analysis to detect: mutations (ancestry, drug dosing, disease predisposition), miRNA (marker for cancer and other diseases), pathogen DNA/RNA (infectious diseases such as HepC, HIV, etc.), microbiome DNA. Further, the sensing device may be used to detect proteins such as biomarkers for a specific disease (cancer, Alzheimer's, infectious diseases, heart disease, cancer etc.) Further, the sensing device may be used to detect small molecules and metabolites to reveal metabolic information (cholesterol). Further, the sensing device may be used to detect biomarkers from exosomes. Further the sensing device may be used to perform microscopy to perform a blood count, analyze cells present in the blood (e.g. circulating tumor cells), identify infectious agents (e.g. malaria) and to detect blood disorders (e.g. sickle cell anemia).

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

The invention claimed is:
1. A fluid analysis device, comprising:
a sensing device for analyzing a fluid sample, comprising
a micro-fluidic component for propagating the fluid sample and a microchip configured for sensing the fluid sample in the micro-fluidic component;

a sealed fluid compartment containing a further fluid, fluid-tight connected to the sensing device and adapted for providing the further fluid to the micro-fluidic component when the sealed fluid compartment is opened, wherein the sealed fluid compartment comprises a sacrificial element adapted to open the sealed fluid compartment towards the micro-fluidic component when the sacrificial element is destroyed;

a heating resistor positioned such that the sacrificial element is destroyed by heating, thereby opening the sealed fluid compartment; and an inlet for providing the fluid sample to the micro-fluidic component.

2. The fluid analyzing device according to claim 1, further comprising a package comprising the sensing device, the sealed fluid compartment and the inlet.

3. The fluid analyzing device according to claim 1, further comprising a movable structure for destructing the sacrificial element.

4. The fluid analyzing device according to claim 1, wherein the heating resistor is positioned in or on the sacrificial element.

5. The fluid analyzing device according to claim 1, wherein the heating resistor is positioned on a substrate comprising the micro-fluidic component.

6. The fluid analyzing device according to claim 1, further comprising a fluid detector positioned to detect the fluid sample when provided in the micro-fluidic component, and wherein the sealed fluid compartment is configured to open when the fluid sample is detected.

7. The fluid analyzing device according to claim 1, wherein the sealed fluid compartment is configured for activating propagation of the fluid sample in the micro-fluidic component when the sealed fluid compartment is opened.

8. The fluid analyzing device according to claim 1, wherein the sensing device comprises:

a silicon fluidic substrate comprising the micro-fluidic component embedded in the silicon fluidic substrate, fluidically connected to the inlet;

a lid attached to the silicon fluidic substrate, at least partly covering the silicon fluidic substrate and at least partly closing the micro-fluidic component, wherein the lid is the microchip.

9. The fluid analyzing device according to claim 8 wherein at least a part of the lid is in contact with the fluid sample when the fluid sample is present in the sensing device.

10. The fluid analyzing device according to claim 8, wherein the lid comprises a transistor layer, the transistor layer being electrically connecting at least one electrical component, the electrical component being at least one of the following: biosensing circuitry, electrodes for sensing purposes, electrodes for fluid manipulation purposes, circuitry for data communication purposes, circuitry for wireless data communication purposes, temperature sensors, heater electrodes for temperature control, fluid sensors and electrodes for fluidic viscosity control and imaging components.

11. A method for sensing a fluid sample, comprising:
providing a fluid analyzing device, wherein the device comprises:

a sensing device for analyzing a fluid sample, comprising a micro-fluidic component for propagating the fluid sample and a microchip configured for sensing the fluid sample in the micro-fluidic component;

a sealed fluid compartment containing a further fluid, fluid-tight connected to the sensing device and adapted for providing the further fluid to the micro-fluidic component when the sealed fluid compartment is opened, wherein the sealed fluid compartment comprises a sacrificial element adapted to open the sealed fluid compartment towards the micro-fluidic component when the sacrificial element is destroyed;

a heating resistor positioned such that the sacrificial element is destroyed by heating, thereby opening the sealed fluid compartment; and an inlet for providing the fluid sample to the micro-fluidic component;

providing a fluid sample to the micro-fluidic component;

mixing the fluid sample with the further fluid contained in the sealed fluid compartment by opening the sealed fluid compartment by heating the sacrificial element thereby providing the further fluid to the micro-fluidic component; and sensing the fluid sample using the sensing device.

12. The method according to claim 11, further comprising detecting a fluid sample being provided to the micro-fluidic component, and wherein the further fluid compartment is opened when the fluid sample is detected.

13. The fluid analyzing device according to claim 8, wherein the microchip is a Complementary Metal-Oxide Semiconductor (CMOS) chip.

14. The fluid analyzing device according to claim 1, wherein the sacrificial element comprises a sealing foil.

\* \* \* \* \*